United States Patent [19]
Castro Pineiro et al.

[11] Patent Number: 5,521,175
[45] Date of Patent: May 28, 1996

[54] BENZODIAZEPINE DERIVATIVES

[75] Inventors: Jose L. Castro Pineiro, Harlow; Mark S. Chambers, Watford; Victor G. Matassa, Furneux Pelham, all of Great Britain

[73] Assignee: Merck Sharp & Dohme Ltd., Hoddesdon, England

[21] Appl. No.: 374,749

[22] PCT Filed: Jul. 28, 1993

[86] PCT No.: PCT/GB93/01600

§ 371 Date: Jan. 26, 1995

§ 102(e) Date: Jan. 26, 1995

[87] PCT Pub. No.: WO94/03447

PCT Pub. Date: Feb. 17, 1994

[30] Foreign Application Priority Data

Jul. 29, 1992 [GB] United Kingdom ............... 9216089
May 5, 1993 [GB] United Kingdom ............... 9309268

[51] Int. Cl.⁶ .................. C07D 401/04; C07D 403/04; A61K 31/55
[52] U.S. Cl. ............................. 514/221; 540/509
[58] Field of Search ..................... 540/509; 514/221

[56] References Cited

U.S. PATENT DOCUMENTS

| | | | |
|---|---|---|---|
| 5,302,591 | 4/1994 | Fletcher et al. | 514/221 |
| 5,360,802 | 11/1994 | Chambers et al. | 514/221 |
| 5,426,185 | 6/1995 | Baldwin et al. | 540/509 |

FOREIGN PATENT DOCUMENTS

| | | |
|---|---|---|
| 0111864A1 | 6/1984 | European Pat. Off. |
| 167919 | 1/1986 | European Pat. Off. |
| 0434364A2 | 6/1991 | European Pat. Off. |
| 434369A1 | 6/1991 | European Pat. Off. |
| 0514133A1 | 11/1992 | European Pat. Off. |
| 539170A1 | 4/1993 | European Pat. Off. |
| WO93/08176 | 4/1993 | WIPO. |

OTHER PUBLICATIONS

"Benzodiazepine Gastrin and Brain Cholecystokinin Receptor Ligands: L–365,260", Mark G. G. Bock, et al., Journal of Medicinal Chemistry, vol. 32, No. 1, Jan. 1989, pp. 13–16.

Primary Examiner—Philip I. Datlow
Attorney, Agent, or Firm—Robert J. North; Melvin Winokur

[57] ABSTRACT

Compounds of Formula (I), and salts and prodrugs thereof, wherein $R^1$ represents $C_{1-6}$alkyl or $C_{3-7}$cycloalkyl; $R^2$ optionally substituted phenyl or $R^2$ represents a group (A) where W is $CH_2$ or $NR^{10}$, and $W^1$ is $CH_2$, or W and $W^1$ each represent 0; $R^3$ is $C_{1-6}$alkyl, halo or $NR^{13}R^{14}$; $R^4$ is H, $C_{1-4}$alkyl, optionally substituted phenyl or optionally substituted benzyl; $R^5$, $R^6$, $R^7$ and $R^8$ are H or $C_{1-4}$alkyl; or any two of $R^4$, $R^5$, $R^6$, $R^7$ and $R^8$ together form a chain $(CH_2)_t$, and any other two of $R^4$, $R^5$, $R^6$, $R^7$ and $R^8$ optionally form a chain $(CH_2)_s$ where s and t are independently 1, 2 or 3; m is 2, 3, 4, 5, 6, 7, 8 or 9; n is 0, 1, 2, 3 or 4; and x is 0, 1, 2 or 3; are CCK and/or gastrin antagonists useful in therapy.

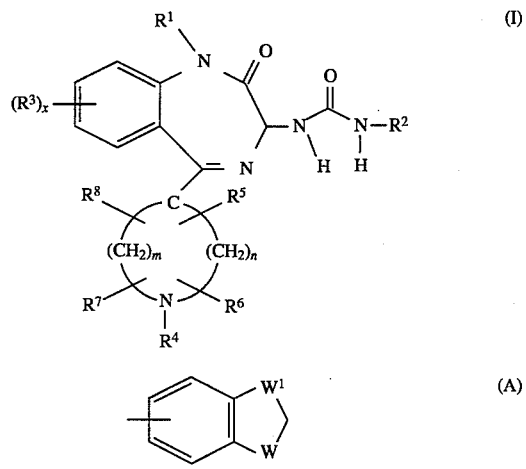

14 Claims, No Drawings

BENZODIAZEPINE DERIVATIVES

This application is a national stage application under 35 USC 371 of application PCT/GB93/01600, filed Jul. 28, 1993.

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem.* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (*Eur. J. Pharmacol.*, 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al.,*J. Med Chem.*, 32, 13–16 (1989)].

European patent application no. 0 167 919 discloses benzodiazepine CCK and gastrin antagonists substituted in the 3-position by, inter alia, a phenyl urea and at the 5-position by an optionally substituted phenyl or pyridyl group.

The present invention provides benzodiazepine compounds of formula (I):

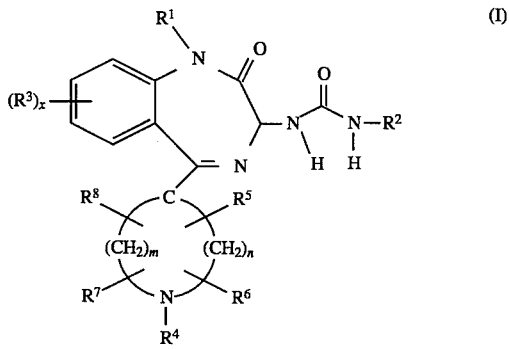

wherein:

R[1] represents $C_{1-6}$alkyl, $C_{3-7}$cycloalkyl, cyclopropylmethyl, $CH_2CO_2R^9$ (where $R^9$ is $C_{1-4}$alkyl) or $CH_2CONR^{13}R^{14}$ (where $R^{13}$ and $R^{14}$ each independently represents H or $C_{1-4}$alkyl, or $R^{13}$ and $R^{14}$ together form a chain $(CH_2)_p$ where p is 4 or 5);

R[2] represents a phenyl group optionally substituted by one or more substituents selected from $C_{1-6}$ alkyl, halo, hydroxy, $C_{1-6}$alkoxy, $(CH_2)_q$-tetrazolyl optionally substituted in the tetrazole ring by $C_{1-4}$alkyl, $(CH_2)_q$-imidazolyl, $(CH_2)_q$triazolyl (where q is 0, 1, 2 or 3), 5-hydroxy-4-pyrone, $NR^{13}R^{14}$, $NR^{10}COR^9$, $NR^{10}CONR^{10'}R^9$ (where $R^{10}$ and $R^{10'}$ are each independently H or $C_{1-6}$alkyl), $CONR^{13}R^{14}$ (where $R^{13}$ and $R^{14}$ are as previously defined), $SO(C_{1-6}$alkyl), $SO_2(C_{1-6}$alkyl), trifluoromethyl, $CONHSO_2R^{11}$, $SO_2NHCOR^{11}$ (where $R^{11}$ is $C_{1-6}$alkyl, optionally substituted aryl, 2,2-difluorocyclopropane or trifluoromethyl), $SO_2NHR^{12}$ (where $R^{12}$ is a nitrogen containing heterocycle ), $B(OH)_2$, $(CH_2)_qCO_2H$ or $(CH_2)_qNR^{10}R^{12}$ (where $R^{12}$ represents tetrazolyl optionally substituted by $C_{1-4}$alkyl); or R[2] represents a group

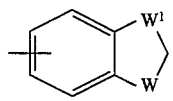

where W represents $CH_2$ or $NR^{10}$, where $R^{10}$ is as previously defined, and $W^1$ represents $CH_2$, or W and $W^1$ each represent O;

R[3] represents $C_{1-6}$alkyl, halo or $NR^{13}R^{14}$, where $R^{13}$ and $R^{14}$ are as previously defined;

R[4] represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl;

R[5], R[6], R[7] and R[8] each independently represent H or $C_{1-4}$alkyl; or any two of R[4], R[5], R[6], R[7] and R[8] together form a chain $(CH_2)_t$, and any other two of R[4], R[5], R[6], R[7] and R[8] optionally form a chain $(CH_2)_s$ where s and t are independently 1, 2 or 3;

m is 2, 3, 4, 5, 6, 7, 8 or 9;

n is 0, 1, 2, 3 or 4;

x is 0, 1, 2 or 3; and pharmaceutically acceptable salts or prodrugs thereof.

It will be appreciated that formula (I) is intended to embrace all possible isomers, including optical isomers, and mixtures thereof, including racemates.

As used herein, the definition of each expression, when it occurs more than once in any structure, is intended to be independent of fts definition elsewhere in the same structure.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs" ed. H. Bungaard, Elsevier, 1985.

As used herein, unless otherwise indicated, alkyl means straight or branched chain saturated hydrocarbon.

When R[1] is $C_{3-7}$cycloalkyl, suitable cycloalkyl groups include cyclopropyl, cyclopentyl and cyclohexyl groups, preferably cyclopropyl.

Halo includes fluoro, chloro, bromo and iodo.

The substituents R[5], R[6], R[7] and R[8] may each be present on any available carbon atom of the azacyclic ring, including the carbon atom attached directly to the benzodiazepine ring.

When any two of R[4], R[5], R[6], R[7] and R[8] combine to form a chain $(CH_2)_t$, an azabicyclic ring system will result which may be bridged, fused, or spiro, preferably bridged. When a further pair of substituents selected from R[4], R[5], R[6], R[7] and R[8] forms a chain $(CH_2)_s$, an azatricyclic ring system will result. Examples of such azabicyclic and azatricyclic ring systems include but are not limited to:

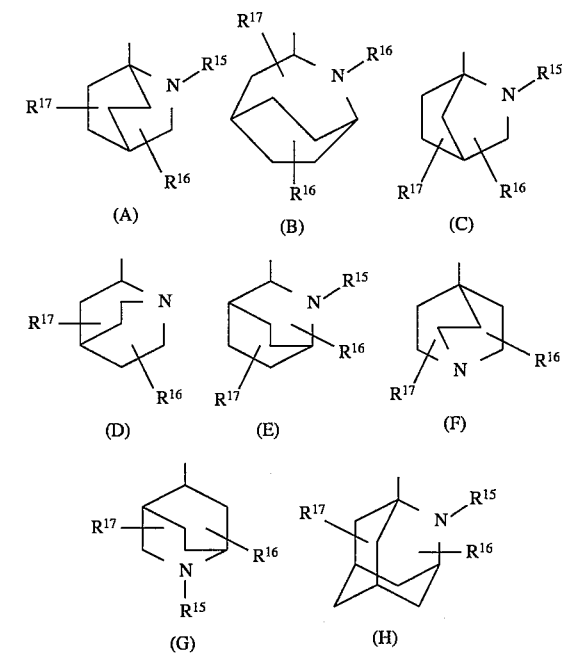

wherein R[15] represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl; and R[16] and R[17] each represent H or $C_{1-4}$alkyl.

A preferred azabicyclic ring system is represented by formula (B ) above.

A subgroup of compounds according to the invention is represented by compounds of formula (I), and salts and prodrugs thereof, wherein R[4] represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl; R[5] and R[6] each independently represent H or $C_{1-4}$alkyl, or R[5] and R[6] together form a chain $(CH_2)_t$, where t is 1, 2 or 3; and R[7] and R[8] are both H.

Within this subgroup there may be identified a further subclass of compounds according to the present invention represented by compounds of formula (IA), and salts and prodrugs thereof:

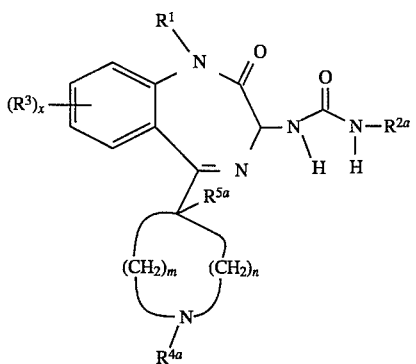

wherein $R^1$, $R^3$, m, n and x are as defined for formula (I), $R^{2a}$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl, 5-hydroxy-4-pyrone, $NR^{13}R^{14}$, $NR^{10}COR^9$, $NR^{10}CONR^{10'}R^9$, $CONR^{13}R^{14}$, $SO(C_{1-6}$alkyl$)$, $SO_2(C_{1-6}$alkyl$)$, trifluoromethyl, $CONHSO_2R^{11}$, $SO_2NHCOR^{11}$, $SO_2NHR^{12}$, $B(OH)_2$ and $(CH_2)_rCO_2H$, where r is zero, 1 or 2; or $R^{2a}$ represents a group

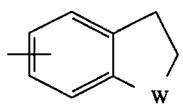

where W represents $CH_2$ or $NR^{10}$;

$R^{4a}$ represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl; and $R^{5a}$ and $R^{6a}$ each independently represent H or $C_{1-4}$alkyl or $R^{5a}$ and $R^{6a}$ together form a chain $(CH_2)_t$.

In compounds of formula (I) it is preferred that $R^1$ is $C_{1-6}$alkyl, such as $C_{1-4}$alkyl, for example, methyl, n-propyl or isobutyl.

Suitable values for $R^{11}$ include methyl, ethyl, i-propyl, t-butyl, phenyl and trifluoromethyl.

When $R^{11}$ is optionally substituted aryl, this will preferably be optionally substituted phenyl.

Suitable substituents include $C_{1-4}$alkyl, $C_{1-4}$alkoxy, halo and trifluoromethyl. Preferred is unsubstituted phenyl or phenyl substituted by $C_{1-4}$alkyl, for example, phenyl substituted by methyl in the ortho position.

When $R^{11}$ is $C_{1-6}$alkyl, it will preferably represent $C_{1-4}$alkyl. Particularly preferred are methyl and iso-propyl, especially iso-propyl.

When $R^2$ is phenyl substituted by $SO_2NHR^{12}$, suitable values of $R^{12}$ include, for example, thiazole, thiadiazole and pyrazine.

Preferably q is zero.

Suitably $R^2$ is phenyl substituted by $C_{1-4}$alkyl, such as methyl, or tetrazolyl, or $R^2$ is 5-indanyl.

When $R^2$ represents monosubstituted phenyl, the substituent will preferably be located at the 3- or 4-position of the phenyl ring, more preferably the 3-position. When $R^2$ represents disubstituted phenyl, the substituents will preferably be located at the 3- and 4-positions. When $R^2$ represents a group

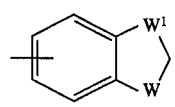

the fused 5-membered ring will preferably be fused across the 3 and 4 positions of the phenyl ring.

Preferably $R^2$ represents phenyl substituted by one or two substituents selected from $C_{1-6}$alkyl, such as methyl or ethyl, halo, such as chloro, bromo, iodo or fluoro, trifluoromethyl and tetrazolyl, or $R^2$ represents 5-indanyl.

More preferably $R^2$ represents phenyl substituted in the 3-position by methyl or tetrazolyl.

Suitable values for $R^3$ include methyl and dimethylamino.

Preferably x is 0 or 1, more preferably 0.

Preferably m is 2, 4, 5 or 6, more preferably 4 or 5.

Preferably n is 0 or 2, more preferably 0.

Preferably $R^4$ is H or methyl.

Preferably $R^5$ and $R^6$ are selected from H and methyl or $R^5$ and $R^6$ together form a hydrocarbon bridge of 1 or 2 carbon atoms.

Preferably $R^7$ and $R^8$ each represent H.

A particularly preferred sub-group of compounds according to the invention is represented by compounds of formula (IB), and salts and prodrugs thereof:

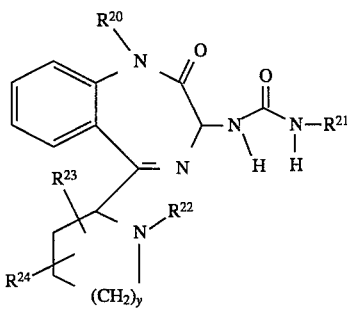

wherein $R^{20}$ is $C_{1-6}$alkyl, preferably $C_{1-4}$alkyl;

$R^{21}$ is 5-indanyl or phenyl substituted by $C_{1-6}$alkyl, halo, trifluoromethyl or tetrazolyl, preferably $C_{1-4}$alkyl, more preferably methyl;

$R^{22}$ is H or $C_{1-6}$alkyl such as methyl;

$R^{23}$ and $R^{24}$ each represent H or methyl or $R^{23}$ and $R^{24}$ together form a hydrocarbon bridge of 1 or 2 carbon atoms; and y is 2 or 3.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from. formula (I) formed, e.g., from non-toxic inorganic or organic salts. For example, such conventional non-toxic salts include those derived from finorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The salts of the present invention can be synthesized from the compounds of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added For oral administration in capsule form, useful diluents include lactose and dried corn starch. When aqueous suspensions are required for oral use, the active ingredient is combined with emulsifying and suspending agents. If desired, certain sweetening and/or flavouring agents may be added For intramuscular, intraperitoneal, subcutaneous and intravenous use, sterile solutions of the active ingredient are usually prepared, and the pH of the solutions should be suitably adjusted and buffered For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonist amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d ). Other routes of administration are also suitable.

For directly inducing analgesia, anaesthesia or loss of pain sensation, the effective dosage preferably ranges from about 100 ng/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by reaction of intermediates of formula (II) with compounds of formula (XIV).

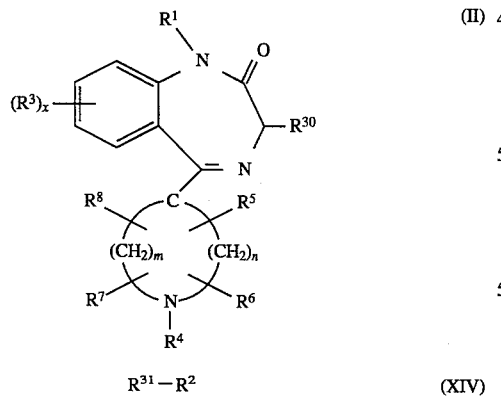

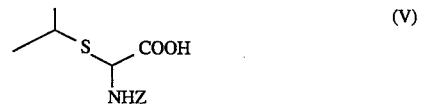

wherein $R^1$, $R^2$, $R^3$, $R^4$, $R^5$, $R^6$, $R^7$, $R^8$, m, n and x are as defined for formula (I) above, except that when $R^4$ is H, it is replaced by a protecting group, one of $R^{30}$ and $R^{31}$ represents $NH_2$ and the other of $R^{30}$ and $R^{31}$ represents $-N=C=O$, followed by deprotection, if required Suitably $R^{30}$ represents $NH_2$ and $R^{31}$ is $-N=C=O$.

Intermediates of formula (II) wherein $R^{30}$ is $-N=C=O$ may be prepared from the corresponding intermediates of formula (II) wherein $R^{30}$ is $NH_2$ by reaction with triphosgene in the presence of a base, such as a tertiary amine, for example, triethylamine. The reaction is conveniently effected in a suitable organic solvent, such as an ether, for example, tetrahydrofuran, suitably at low temperature, such as about 0° C.

Intermediates of formula (II) wherein $R^{30}$ is $NH_2$ may be prepared from compounds of formula (III)

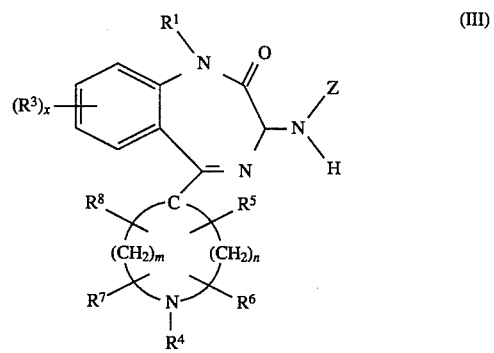

wherein $R^3$, $R^4$, $R^5$, $R^6$, $R^7$, $R^8$, m, n and x are as defined for formula (II) and Z is a protecting group; by reaction with a reagent suitable to introduce the group $R^1$, for example a halide of formula $R^1$Hal where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene, followed by removal of the Z protecting group.

Compounds of formula (III) may be prepared from compounds of formula (IV)

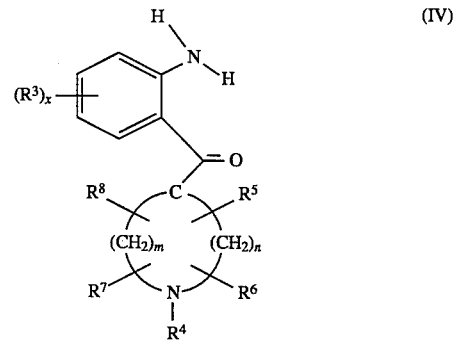

wherein $R^3$, $R^4$, $R^5$, $R^6$, $R^7$, $R^8$, m, n and x are as defined for formula (II) by a reaction sequence comprising:

(i) reaction with a compound of formula (V)

$$\underset{NHZ}{\overset{}{\underset{|}{>\!\!\!-\!\!S\!-\!\!\!-\!COOH}}}$$ (V)

wherein Z is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC) or bis(2-oxo-3-oxazolidinyl)phosphinic chloride (BOP-Cl).

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran.

(iii) Treatment with an organic acid, for presence of an ammonium salt, for example ammonium acetate.

Compounds of formula (IV) may be prepared from compounds of formula (VI)

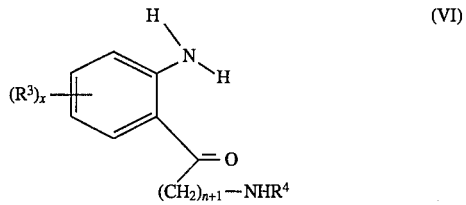

wherein $R^3$, $R^4$, m, n and x are as defined for formula (II) and the chain $(CH_2)_{n+1}$ may be substituted by one or more of $R^5$, $R^6$, $R^7$ and $R^8$, by reaction with a compound of formula Hal-$(CH_2)_m$-Hal, where Hal is halo, such as bromo or iodo, m is as previously defined and the chain $(CH_2)_m$ may be substituted by one or more of $R^5$, $R^6$, $R^7$ and $R^8$ as defined for formula (I), in the presence of a base.

Suitable bases of use in the reaction include alkali metal hydrides such as, for example, sodium hydride.

The reaction is conveniently effected in a suitable organic solvent, such as, for example, dimethylformamide, preferably at low temperature, such as about 0° C.

Alternatively, compounds of formula (IV) may be prepared by oxidation of the corresponding alcohols of formula (VII)

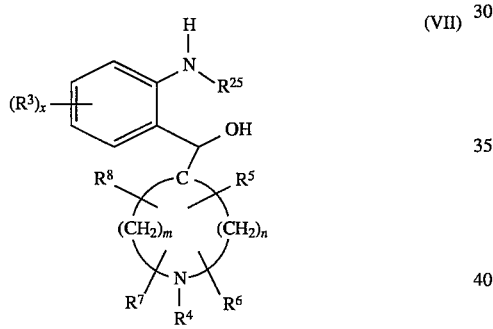

wherein $R^3$, $R^4$, $R^5$, $R^6$, $R^7$, $R^8$, m, n and x are as defined for formula (I) and $R^{25}$ represents a protecting group, followed by deprotection.

The reaction is preferably effected using a mild catalytic oxidant, such as tetrapropylammonium perruthenate.

Further alternative methods for the preparation of compounds of formula (IV) will be apparent to those skilled in the art and are described in the accompanying Examples.

Compounds of formula (VI) may be prepared from the corresponding compounds of formula (VIII)

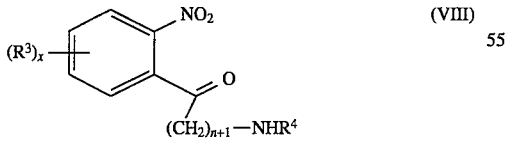

wherein $R^3$, $R^4$, m, n and x are as defined for formula (II), by reduction.

Suitably the reaction is effected by hydrogenation in the presence of a suitable catalyst, such as a nobel metal catalyst, for example palladium, which may be supported, for example, on carbon.

The reaction is conveniently carried out in a suitable organic solvent, such as an alcohol, for example, ethanol.

Compounds of formula (VIII) may be prepared from compounds of formula (IX):

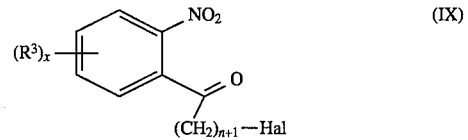

wherein $R^3$, $R^4$, n and x are as previously defined, by a reaction sequence suitable to introduce the group —$NHR^4$. For example, the compound of formula (IX) may be treated with hexamethylenetetramine, followed by an acid, such as an aqueous mineral acid, for example hydrochloric acid, to introduce the group —$NH_2$. The —$NH_2$ group may then be transformed by conventional methods to a group —$NHR^4$, where $R^4$ is as defined for formula (II), or a suitable protecting group. Suitable reagents and methods are described in the accompanying examples, or will be readily apparent to those skilled in the art.

Compounds of formula (IX) are commercially available or may be prepared from commercially available compounds by known methods.

Compounds of formula (VII) may be prepared by reaction of a compound of formula (X) with a compound of formula (XI)

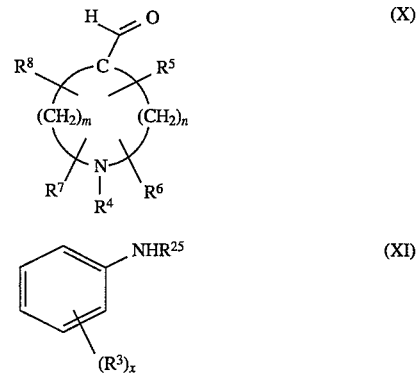

wherein $R^3$, $R^5$, $R^6$, $R^7$, $R^8$, m, n and x are as defined for formula (I), $R^4$ is as defined for formula (I) except that if $R^4$ is H it is replaced by a protecting group, and $R^{25}$ is as previously defined, in the presence of a base.

Suitable bases of use in the reaction include alkyl lithiums, such as, for example, t-butyl lithium. The reaction is conveniently effected in a suitable organic solvent, such as an ether, for example, tetrahydrofuran, at low temperature, such as about −80° to −30° C.

Compounds of formula (X) may be prepared by reduction of compounds of formula (XII)

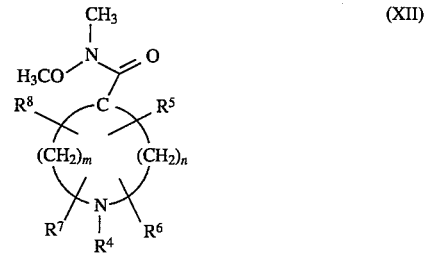

wherein $R^4$, $R^5$, $R^6$, $R^7$, $R^8$, m and n are as defined for formula (X) above.

Suitable reducing agents for use in the reaction include hydride reducing agents such as, for example, diisobutylaluminium hydride. The reaction is conveniently effected in a suitable organic-solvent, such as a hydrocarbon, for example, toluene, at low temperature, such as about −40° to −30° C.

Compounds of formula (XII) may be prepared from compounds of formula (XIII)

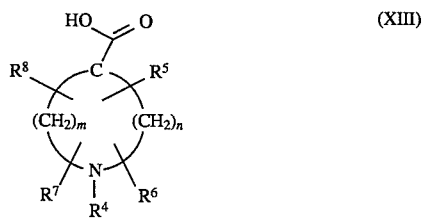

wherein $R^4$, $R^5$, $R^6$, $R^7$, $R^8$, m and n are as defined for formula (X), by reaction with the compound $HN(OCH_3)CH_3$, or the hydrochloride salt thereof, in the presence of a base and a coupling reagent.

Suitable bases of use in the reaction include tertiary amines such as, for example, triethylamine. Suitable coupling reagents include carbodiimides, such as, for example, 1,3-dicyclohexylcarbodiimide.

Compounds of formula (XIII) are commercially available or may be prepared from commercially available compounds by procedures well known to those skilled in the art.

According to an alternative procedure, intermediates of formula (IV) may be prepared by reaction of compounds of formula (XI) with compounds of formula (XII), followed by deprotection. Details of this procedure may found in the accompanying examples.

Intermediates of formulae (II) and (III) are novel compounds and form a further aspect of the present invention.

Thus, in a further or alternative aspect, the present invention provides an intermediate of formula (M)

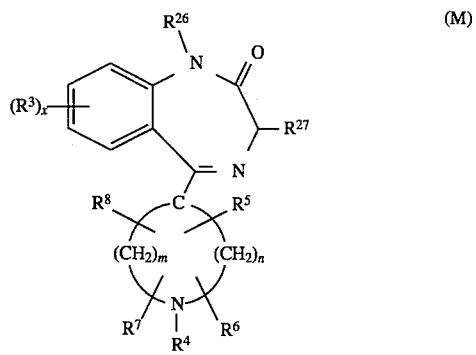

wherein $R^3$, $R^4$, $R^5$, $R^6$, $R^7$, $R^8$, m, n and x are as defined for formula (I); $R^{26}$ is H or $R^1$ as defined for formula (I); and $R^{27}$ is $NH_2$, —N=C=O or NHZ (where Z is a protecting group).

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

INTERMEDIATE I 3-(Benzylcarbonylamino)-5-(1-tert-butyloxycarbonyl piperidin-2-yl)-1,3-dihydro-1-(1-propyl)-2H-1,4-benzodiazepim-2-one. Diastereomers A and B 1. 2-(N-tert-Butyloxycarbonylamino)-2'-nitroacetophenone To a stirred mixture of finely powdered hexamethylenetetromine (12.7 g) in anhydrous chlorobenzene (80 ml) was added via cannula a solution of 2-bromo-2'-nitroacetophenone (20 g) in anhydrous chlorobenzene (80 ml) over 5 minutes, under a nitrogen atmosphere. The resulting mixture was heated to 50°–57° C. for 4 hours before it was allowed to cooled to room temperature overnight. The precipitated solid was collected by filtration and it was washed with absolute ethanol (1×70 ml and 1×25 ml) and diethyl ether (1×200 ml). This pale yellow powder was added portionwise to a mixture of 95% ethanol (75 ml) and concentrated hydrochloric acid (35 ml) over 2 minutes and the resulting suspension was stirred at room temperature for 22 hours. After being cooled to 5° C., the solid was collected by filtration, washed with diethyl ether (2×50 ml) and dried under high vacunm for 45 minutes. The white solid thus obtained was suspended in anhydrous dichloromethane (500 ml) and treated with anhydrous triethylamine (6 ml) before di-tert-butyl dicarbonate (25.5 g) was added in one portion. Additional anhydrous triethylamine (10 ml) was then added and the mixture was stirred at room temperature for 45 minutes, under nitrogen. The reaction mixture was washed with 10% aqueous citric acid (1×100 ml and 1×70 ml), water (1×100 ml), brine (1×100 ml), dried ($MgSO_4$) and concentrated Flash chromatography (silica gel, hexane-ethyl acetate, 60:40) of the residue gave the title compound (12.25 g) as a yellow oil which solidifies on standing; $\delta_H$ (250 MHz, $CDCl_3$) 8.17 (1H, dd, J=8.2 and 0.9 Hz, Ar—H), 7.76 (1H, dt, J=7.4 and 1.1 Hz, Ar—H), 7.64 (1H, dt, J=8.2 and 1.6 Hz, Ar—H), 7.51 (1H, br d, J=7.4 HZ, Ar—H), 5.25 (1H, br s, —NH—), 4.33 (2H, d, J=5.6 Hz, —$CH_2$—), 1.40 (9H, s, t-Bu); m/z (CI)280 (M⁻).

2. 2 (N-tert-Butyloxycarbonylamino)-2'-aminoacetophenone

A solution of 2-(N-tert-butyloxycarbonylamino)-2'-nitroacetophenone (10.5 g) in a mixture of absolute ethanol (200 ml), ethyl acetate (60 ml) and water (20 ml) was hydrogensted at 26 psi over 10% palladium on carbon (2.06 g) for 7 minutes. The catalyst was removed by filtration, washed with absolute ethanol (50 ml) and solvents were removed under vacuum. The remaining residue was triturated with a mixture of hexane and diethyl ether (1:1; 80 ml) to give the title compound (7.5 g) as a pale yellow solid. The mother liquors were concentrated and purified by flash chromatography (silica gel, hexane-ethyl acetate, 60:40) to give a further 0.95 g of the required product; $\delta_H$ (250 MHz, CDCl$_3$), 7.63 (1H, d, J=8.3 Hz, Ar—H), 7.29 (1H, dt, J=8.0 and 1.5 Hz, Ar—H), 6.70–6.63 (2H, m, Ar—H), 5.57 (1H, br s, —NH—), 4.61 (2H, d, J=4.4 Hz, —CH$_2$—), 1.48 (9H, s, t-Bu); m/z (CI) 251 (M$^+$+1).

3. [2-Aminophenyl][2(R,S)-1-tert-butyloxycarbonylpiperidin-2-yl]methanone

To a cooled (−3° C.) and stirred solution of the product from the previous step (7.97 g) in anhydrous dimethylformamide (95 ml) was added sodium hydride (60% dispersion in oil; 2.67 g) in one portion, under a nitrogen atmosphere. After 20 minutes of stirring, 1,4-dibromobutane (4.18 ml) was added dropwise over 2 minutes and stirring was continued at −3° C. for 1.5 hours. The reaction was quenched by addition of ethyl acetate (150 ml), saturated aqueous ammonium chloride solution (280 ml) and water (100 ml), and the organic phase was decanted off. The aqueous layer was extracted with ethyl acetate (2×250 ml) and the combined organic phases were washed with brine (2×100 ml), dried (MgSO$_4$) and concentrated Flash chromatography (silica gel, hexane-diethyl ether, 60:40) of the residue gave the title compound (3.96 g) as a pale yellow solid; $\delta_H$ (250 MHz, DMSO-d$_6$)7.74 (1H, d, J=7.8 Hz, Ar—H), 7.27–7.20 (1H, m, Ar—H), 7.09 (2H, br s, —NH$_2$), 6.78 (1H, dd, J=8.4 and 1.1 Hz, Ar—H), 5.52 (1H, br s, —CHCO—), 3.88–3.76 (1H, m, —CHN—), 3.31–3.16 (1H, m, —CHN—), 2.04–1.06 (15H, m, —CH$_2$- and t-Bu); m/z (CI)305 (M$^+$+1).

4. 3-(Benzyloxycarbonylamino)-5-(1-tert-butyloxycarbonylpiperidin- 2-yl)-1,3-dihydro-2H-1,4-benzodiazepin-2-one. Diastereomers A and B To a cooled (5° C.) and stirred solution of [2-aminophenyl][2(R,S) )-1-tert-butyloxycarbonylpiperidin-2-yl]methanone (3.25 g) and α-(isopropylthio)-N-(benzyloxycarbonyl) glycine (4.23 g) in anhydrous dichloromethane (50 ml) was added anhydrous triethylamine (4.16 ml) followed by bis(2-oxo-3-oxazolidinyl) phosphinic chloride (3.80 g) in one portion. The mixture was stirred at 5° C. for further 5 minutes and at room temperature for 55 minutes before it was diluted with diethyl ether (200 ml). The organic solution was washed with 10% aqueous citric acid (2×40 ml), water (1×40 ml), saturated aqueous sodium bicarbonate (1×40 ml), water (1×40 ml), brine (1×40 ml), then dried (MgSO$_4$) and concentrated. Flash chromatography (silica gel, hexane-diethyl ether, 60:40) of the residue gave the (isopropylthio)glycinamide derivative (2.78 g) as a pale yellow oil: $\delta_H$ (250 MHz, DMSO-d$_6$)11.44–11.18 (1H, m, —HN—), 8.52–8.26 (2H, m), 8.08–7.98 (1H, br d), 7.70–7.58 (1H, br t), 7.44–7.20 (6H, m), 5.62–5.55 (1H, m), 5.50–5.38 (1H, m), 5.10 (2H, s), 3.88–3.70 (1H, m), 3.28–3.02 (2H, m), 2.00–1.10 (21H, m); m/z (CI) 569 (M$^-$).

Ammonia gas was bubbled for 1.5 hours through a cooled (−5° C.) and stirred solution of the (isopropylthio)glycinamide derivative previously obtained (2.77 g) in anhydrous tetrahydrofuran (100 ml). Mercury (II) chloride (2.64 g) was then added and ammonia bubbling was continued for a further 3 hours 15 minutes at −3° C. The reaction mixture was filtered through hyflo filter aid to remove solids and the filtrate was concentrated under vacuum. The remaining residue was suspended in glacial acetic acid (40 ml), ammonium acetate (1.5 g) was added and the mixture was stirred at room temperature for 19 hours and at 50° C. for 1.5 hours, under a nitrogen atmosphere. Solvents were removed under vacuum and the residue was partitioned between 2N sodium hydroxide (80 ml) and diethyl ether (200 ml). The aqueous phase was extracted with diethyl ether (1×200 ml) and the combined organic solutions were washed with brine (2×50 ml), dried (MgSO$_4$) and concentrated Flash chromatography (silica gel, hexane-diethyl ether, 20:80) of the residue gave 577 mg (25%) of the title compound (diastereomer A. less polar) and 940 mg (40%) of the title compound (diastereomer B. more polar) as white solids. Both diastereomers had: m/z (CI) 493 (M$^+$+1).

5. 3-(Benzyloxycarbonylamino)-5-(1-tert-butyloxycarbonylpiperidin- 2-yl)-1,3-dihydro-1-(1-propyl)-2H-1,4-benzodiazepin-2-one. Diastereomers A and B

DIASTEREOMER A

To a cooled and stirred solution of 3-(benzyloxycarbonylamino)-5-( 1-tert-butyloxycarbonylpiperidin-2-yl)- 1,3-dihydro-2H -1,4-benzodiazepin-2-one (diastereomer A; 570 mg) in a mixture of anhydrous tetrahydrofuran (6 ml) and anhydrous dimethylfomsmide (3 ml) was added sodira hydride (60% dispersion in oil; 54 mg) and the resulting mixture was stirred at this temperature for 12 minutes, under a nitrogen atmosphere. 1-Iodopropane (230 µl) was then added and the mixture was allowed to warm to room temperature and stirred for 1 h 50 minutes. Water (50 ml) was added and products were extracted with diethyl ether (2×70 ml). The combined organic phases were washed with brine (2×35 ml), dried (MgSO$_4$) and concentrated Flash chromtography (silica gel, hexane-ethyl acetate, 70:30) of the-residue gave the title compound (diastereomer A) (421 mg) as a pale yellow glass; $\delta_H$ (250 MHz, CDCl$_3$) 7.66 (1H, br s), 7.52–7.15 (9H, m), 6.66–6.52 (1H, br d), 5.68–5.46 (1H, br s), 5.20–5.06 (3H, m), 4.18–4.04 (1H, m), 3.84–3.55 (2H, m), 2.56–2.42 (1H, m), 2.20–1.94 (1H, br s), 1.80–1.30 (16H, m), 0.90 (3H, t, J=7.3 Hz); m/z (CI) 534 (M$^-$).

DIASTEREOMER B

The title compound (diastereomer B) was prepared from 3-(benzyloxycarbonylamino)-5-(1-tert-butyloxycarbonylpiperidin-2-yl)- 1,3-dihydro-2H-1,4-benzodiazepin-2-one (diastereomer B) using a similar method to that described above for diastereomer A; white foam; $\delta_H$ (250 MHz, CDCl$_3$)7.84–7.15 (9H, m), 6.40 (1H, br d, J=7.3 Hz), 5.54–5.30 (1H, br s), 5.13 (1H, br d, J=7.3 Hz), 5.07 (2H, s), 4.28–4.15 (1H, m), 4.02–3.80 (1H, br s), 3.63–3.51 (1H, m), 3.50–3.24 (1H, br s), 1.78–1.00 (17H, m), 0.86 (3H, t, J=7.3 Hz); m/z (CI) 534 (M$^-$).

INTERMEDIATE 2

3-Amino-5-(1-tert-butyloxycarbonylnineridin-2-yl)-1,3-dihydro-1-(1-propyl)-2H- 1,4-benzodiazepin-2-one. Diastereomer A To a stirred suspension of 10% palladium on carbon (98 mg) in a mixture of methanol and 90% formic acid (95.5:4.5; 9 ml) was added dropwise via cannula a solution of Intermediate 1 (diastereomer A; 310 mg) in the same solvent (30 ml) over 12 minutes, under a nitrogen atmosphere. After being stirred at room temperature for 30 minutes, the catalyst was removed by filtration, washed with methanol (2×25 ml) and the filtrate was neutralised with 10% aqueous sodium carbonate (~30 ml) before the organic solvents were removed under vacuum. The residue was diluted with water (10 ml) and saturated aqueous potassium carbonate (3 ml) and products were extracted with ethyl acetate (2×100 ml). The combined organic solutions were washed with brine (1×30 ml), dried (Na$_2$SO$_4$) and concentrated to give the title compound (diastereomer A) (235 mg) as a white solid; $\delta_H$ (250 MHz, CDCl$_3$) 7.70–7.56 (1H, m), 7.49–7.42 (1H, m), 7.33 (1H, d, J=7.4 Hz), 7.19–7.12 (1H, m), 5.66–5.44 (1H, br s), 4.30 (1H, d, J=1.5 Hz), 4.18–4.05 (1H, m), 3.73–3.63 (2H, m), 2.62–2.50 (1H, m), 2.10–1.26 (19H, m), 0.91 (3H, t, J=7.4 Hz); m/z (CI)401 (M$^+$+1).

INTERMEDIATE 3

3-Amino-5-(1-tert-butyloxycarbonylpiperidin-2-yl)-1,3-dihydro-1-(1-propyl)-2H- 1,4-benzodiazepin-2-one. Diastereomer B The title compound (diastereomer B) was prepared in quantitative yield from Intermediate I (diastereomer B) using a similar method to that described for Intermediate 2; white foam; $\delta_H$ (360 MHz, CDCl$_3$) 7.84–7.60 (1H, br s), 7.50 (1H, t, J=8.1 Hz), 7.34 (1H, d, J=8.1 Hz), 7.25 (1H, t, J=7.4 Hz), 5.52–5.30 (1H, br s), 4.30–4.18 (2H, m), 3.96–3.83 (1H, m), 3.64–3.40 (2H, m), 1.93 (—NH$_2$, br s), 1.76–1.10 (17H, m); m/z (CI) 401 (M$^+$+1).

EXAMPLE 1

N-[2,3-Dihydro-2-oxo-5-(piperidin-2-yl)-1-(1-propyl)-1H-1,4-benzodiazepin-3-yl]-N'-[3-methylphenyl]urea hydrochloride. Diastereomer A 1. N-[5-(1-tert-Butyloxycarbonylpiperidin-2-yl)-2,3-dihydro-2-oxo-1-(1-propyl)-1H-1,4-benzodiazepin-3-yl]-N'-[3-methylphenyl]urea. Diastereomer A To a stirred solution of Intermediate 2 (230 mg) in anhydrous tetrahydrofuran (7 ml) was added dropwise m-tolyl isocyanate (81.5 μl) over 2 minutes, under a nitrogen atmosphere. After being stirred at room temperature for 2 hours 45 minutes, the mixture was diluted with methanol (5 ml) and solvents were removed under vacuum. The remaining residue was triturated with a mixture of hexane (10 ml) and diethyl ether (1 ml) to give the title compound (diastereomer A) (289 mg) as a white solid; mp 189°–195° C.; $\delta_H$ (250 MHz, CDCl$_3$) 7.76–7.60 (1H, br s), 7.51–7.44 (1H, m), 7.35 (1H, d, J=8.3 Hz), 7.26–7.06 (,1H, m), 6.88 (1H, d, J=7.5 Hz), 6.76–6.60 (2H, m), 5.70–5.46 (1H, br s), 5.37 (1H, br d, J=7.7 Hz), 4.20–4.06 (1H, m) 3.80–3.60 (2H, m), 2.58–2.46 (1H, m), 2.31 (3H, s), 2.20–2.00 (1H, br s), 1.80–1.26 (16H, m), 0.90 (3H, t, J=7.3 Hz); m/z (CI) 533 (M$^-$).

2. N-[2,3-Dihydro-2-oxo-5-(piperidin-2-yl)-1-(1-propyl)-1H-1,4-benzodiazenin- 3-yl]-N'-[3-methylphenyl]ureo hydrochloride. Diastereomer A A solution of the product from the previous step (270 mg) in a mixture of dichloromethane (10 ml) and trifluoroacetic add (4 ml) was allowed to stand at room temperature for 15 minutes before additional trifluoroacetic acid (4 ml) was added. After a further 20 minutes, solvents were removed under vacuum and the residue was azeotroped with methanol (2×15 ml) before it was partitioned between 10% aqueous potassium carbonate (15 ml) and ethyl acetate (75 ml). The aqueous phase was extracted with ethyl acetate (1×75 ml) and the combined organic solutions were washed with brino (1×30 ml), dried (Na$_2$SO$_4$) and concentrated. Flash chromatography (silica gel, dichloromethane-methanol, 90:10) of the remaining yellow oil gave the title compound free base (diastereomer A) (110 mg) as a white solid The hydrochloride salt was prepared; mp 214°–218° C. (methanol-diethyl ether); $\delta_H$ (360 MHz, DMSO-d$_6$) 9.34–9.22 (2H, m), 7.76–7.46 (1H, br s), 7.80 (1H, d J=7.9 Hz), 7.73 (1H, d, J=7.8 and 1.2 Hz), 7.64 (1H, d, J=7.8 Hz), 7.49, (1H, d, J=8.2 Hz), 7.44 (1H, t, J=7.9 Hz), 7.19 (1H, s), 7.15–7.06 (2H, m), 6.73 (1H, d, J=7.3 Hz), 5.13 (1H, d, J=8.2 Hz), 4.50–4.38 (1H, br s), 3.88–3.74 (2H, m), 3.17 (1H, br d, J=12.9 Hz), 3.04–2.90 (1H, br s), 2.41 (1H, br d, J=11 Hz), 2.22 (3H, s), 1.90–1.52 (6H, m), 0.86 (3H, t, J=7.3 Hz); m/z (CI) 433 (M$^-$). (Found: C, 63.73; H, 6.81; N, 14.81. C$_{25}$H$_{31}$N$_5$O$_2$×1.0 HCl requires: C, 63.89; H, 6.86; N, 14.90%).

EXAMPLE 2

N-[2,3-Dihydro-2-oxo-5-(piperidin-2-yl)-1-(1-propyl)-1H-1,4,benzodiazepin-3-yl]-N'-[3-methylphenyl]urea hydrochloride. Diastereomer B 1. N-[5-(1-tert-Butyloxycarbonylpiperidin-2-yl)-2,3-dihydro-2-oxo- 1-(1-propyl)-1H-1,4-benzodiazepin-3-yl]-N'-[3-methylphenyl]urea. Diastereomer B The title compound (diastereomer B) was prepared in 98% yield from Intermediate 3 using a similar method to that described for Example 1 (step 1); white solid; mp 206°–213° C. (hexane-diethyl ether); $\delta_H$ (250 MHz, CDCl$_3$) 7.76–7.06 (7H, m), 6.86 (1H, br d, J=7.8 Hz), 6.62 (1H, br s) 6.35 (1H, br d, J=8.0 Hz), 5.50–5.38 (2H, m), 4.30–4.20 (1H, m), 3.98–3.84 (1H, m), 3.66–3.52 (1H, m), 3.44–3.22 (1H, br s), 2.31 (3H, s), 1.80–1.04 (17H, m), 0.86 (3H, t, J=7.3 Hz); m/z (CI), 533 (M$^-$).

2. N-[2-Dihydro-2-oxo-5-(piperidin-2-yl)-1-(1-propyl)-1H-1,4-benzodiazepin-3-yl]-N'-[3-methylphenyl]urea hydrochloride. Diastereomer B The title compound free base (diastereomer B) was prepared from the product of the previous step using a similar method to that described for Example 1 (step 2). The hydrochloride salt was prepared and recrystallized from a mixture of methanol and diethyl ether; mp 191°–195° C.; $\delta_H$ (360 MHz, CDCl$_3$) 10.65 (1H, s), 9.27 (1H, br d), 9.02 (1H, d, J=8.6 Hz), 8.89 (1H, br q), 7.83 (1H, d, J=6.8 Hz), 7.54 (1H, t, J=7.2 Hz), 7.40–7.24 (4H, m), 6.98 (1H, t, J=7.7 Hz), 6.67 (1H, d, J=7.5 Hz), 5.39 (1H, d, J=8.6 Hz), 4.32–4.23 (1H, m), 3.96 (1H, br t), 3.54–3.42 (1H, m), 3.11 (1H, br d, J=12.6 Hz), 2.87 (1H, br q, J=11 Hz), 2.23 (3H, s), 1.92–1.76 (1H, m), 1.70–1.44 (2H, m), 1.30–1.02 (4H, m), 0.77 (3H, t, J=7.3 Hz), 0.46–0.30 (1H, m); m/z (CI), 433 (M$^-$) (Found: C, 62.38; H, 6.81; N, 14.29. C$_{25}$H$_{31}$N$_5$O$_2$×1.0 HCl×0.7 H$_2$O requires: C, 62.22; H, 6.98; N, 14.51%).

EXAMPLE 3

N-[2,3-Dihydro-5-(1-methylpiperidin-2-yl)-2-oxo-1-(1propyl)-1H-1,4-benzodiazepin-3-yl]-N'-[3-methylphenyl]urea hydrochloride. Diastereomer B To a stirred solution of the product from Example 2 (diastereomer B, free base) (100 mg) in a mixture of methanol (5 ml) and glacial acetic acid (53 μl) was added sodium cyanoborohydride (15 mg) followed by a solution of formaldehyde (38% w/v aqueous solution; 23 μl) in methanol (1 ml). The mixture was stirred at room temperature for 40 minutes, then diluted with saturated aqueous potassium carbonate (2 ml) and the methanol was removed under vacuum. The residue was diluted with water (15 ml) and products were extracted with dichloromethane (2×40 ml), washed with brine (1×20 ml), dried (Na$_2$SO$_4$) and concentrated. Flash chromatography (silica gel, dichloromethane-methanol, 90:10) of the residue gave the title compound free base (diastereomer B) (96 mg) as a white solid The hydrochloride salt was prepared; mp 180°–187° C. (methanol-diethyl ether); $\delta_H$ (360 MHz, DMSO-d$_6$) 9.62 (1H, br s), 9.30 (1H, s), 8.01 (1H, d, J=7.8 Hz), 7.82–7.72 (2H, m), 7.59 (1H, d, J=7.2 Hz), 7.51 (1H, br t, J=8.0 Hz), 7.22–7.06 (3H, m), 6.74 (1H, d, J=7.4 Hz), 5.08 (1H, d, J=7.2 Hz), 4.92–4.80 (1H, m), 4.30–4.21 (1H, m), 3.80–3.69 (1H, m), 3.48–3.38 (1H, m), 3.28–3.10 (1H, m), 2.97 (3H, br s), 2.22 (3H, s), 1.86–1.66 (4H, m), 1.56–1.18 (4H, m), 0.75 (3H, t, J=7.3 Hz); m/z (CI), 447 (M$^-$). (Found: C, 62.30; H, 7.41;

N, 13.68. $C_{26}H_{33}N_5O_2 \times 1.0$ HCl×1.0 $H_2O$ requires: C, 62.20; H, 7.23; N, 13.95%).

INTERMEDIATE 4

3-Amino-5-(1-tert-butyloxycarbonyl-5,5-dimethyl- 2,3,4,5,6,7-hexahydro-1H-azepin-2-yl)-1,3-dihydro-1-(1-propyl)-2H-1,4-benzodiazepin-2-one. Diastereomer B 1. [2-Aminophenyl][2(R,S)-1-tert-butyloxycarbonyl-5,5-dimethyl-2,3,4,5,6,7-hexahydro- 1H-azepin2-yl]methanone The title compound was prepared in 21% yield from 2-(N-tert-butyloxycarbonylamino)- 2'-aminoacetophenone and 1,5-dibromo- 3,3-dimethylpentane (*Chem. Pharm. Bull.*, 1985, 33, 5048) following a similar method to that described for Intermediate 1 (step 3); thick yellow oil; $\delta_H$ (360 MHz, CDCl$_3$) 7.88 and 7.74 (1H, two d, J=8.1 Hz), 7.26 (1H, m), 6.65 (2H, t, J=8.0 Hz), 6.18 (2H, s), 5.53 and 5.30 (1H, two dd, J=12.2 and 5.7 Hz), 4.08 and 3.85 (1H, two m), 3.23 (1H, m), 2.05–1.92 (1H, m), 1.85–1.69 (1H, m), 1.56–1.43 (4H, m), 1.46 and 1.27 (9H, two s), 0.96–0.92 (6H, four s); m/z (CI) 347 (M$^+$+1). (Found: m/z, 346.2251. $C_{20}H_{30}N_2O_3$ requires m/z, 346.2256).

2. 3-(Benzyloxycarbonylamino)-5-(1-tert-butyloxycarbonyl-5,5-dimethyl-2,3,4,5,6-hexahydro- 1H-azepin-2-yl)-1,3-dihydro-2H-1,4-benzodiazepin-2-one. Diastereomers A and B The title compounds were prepared from [2-aminophenyl][2(R,S)-1-tert-butyloxycarbonyl-5,5-dimethyl-2,3,4,5,6-hexahydro-1H-azepin-2-yl]methanone (2.08 g) following a similar method to that described for Intermediate 1 (step 4). The crude product was purified by flash chromatography (silica gel, hexane-diethyl ether, 90:10 to 80:20) to give the title compound (Diastereomer A: less polar: 300 mg) and the title compound (Diastereomer B: more polar: 1.3 g); both diastereomers showed: m/z (CI) 535 (M$^+$+1).

3. 3-(Benzyloxycarbonylamino)-5-(1-tert-butyloxycarbonyl-5,5-dimethyl-2,3,4,5,6-hexahydro- 1H-azepin-2-yl)-1,3-dihydro-1-(1-propyl)- 2H-1,4-benzodiazepin-2-one. Diastereomer B The title compound was prepared from 3-(benzyloxycarbonyl-amino)- 5-(1-tert-butyloxycarbonyl-5,5-dimethyl-2,3,4,5,6-hexahydro- 1H-azepin-2-yl)-1,3-dihydro-2H-1,4-benzodiazepin-2-one (Diastereomer B) following a similar method to that described for Intermediate 1 (step 5); colourless thick oil; $\delta_H$ (250 MHz, CDCl$_3$) 8.08 and 7.67 (1H, two d, J=7.3 Hz), 7.56–7.49 (1H, m), 7.38–7.28 (7H, m), 6.34 (1H, m), 5.19–5.06 (4H, m), 4.28 (1H, m), 3.97 and 3.75 (1H, two m), 3.58 (1H, m), 3.26–2.92 (1H, m), 1.72–1.25 (8H, m), 1.46 and 1.44 (9H, two s), 0.90–0.83 (9H, m); m/z (CI)577 (M$^+$+1).

4. 3-Amino-5-(1-tert-butyloxycarbonyl-5,5-dimethyl-2,3,4,5,6-hexahydro- 1H-azepin-2-yl)-1,3-dihydro-1-(1-propyl)-2H-1,4-benzodiazepin-2-one. Diastereomer B The title compound was prepared from the product of the previous step using a similar method to that described for Intermediate 2; white foam; $\delta_H$ (250 MHz, CDCl$_3$) 8.02 and 7.67 (1H, two d, J=6.4 Hz), 7.56–7.45 (1H, m), 7.37–7.24 (2H, m), 5.18–5.00 (1H, m), 4.35–4.24 (2H, m), 3.97 and 3.75 (1H, two m), 3.58 (1H, m), 3.22–3.00 (1H, m), 1.91–1.21 (10H, m), 1.50 and 1,47 (9H, two s), 0.90–0.82 (9H, m); m/z (CI) 443 (M$^+$+1).

INTERMEDIATE 5

3-Amino-5-(1-tert-butyloxycarbonyl-5,5-dimethyl-2,3,4,5,6-hexahydro- 1H-azepin-2-yl)-1,3-dihydro-1-methyl-2H-1,4-benzodiazepin-2-one. Diastereomer B 1. 3-(Benzyloxycarbonylamino)-5-(1-tert-butyloxycarbonyl-5,5-dimethyl-2,3,4,5,6-hexahydro-1H-azepin-2-yl)-1,3-dihydro-1-methyl-2H-1,4-benzodiazepin-2-one. Diastereomer B The title compound was prepared from 3-(benzyloxycarbonylamino)-5-(1-tert-butyloxycarbonyl-5,5-dimethyl- 2,3,4,5,6-hexahydro-1H-azepin-2-yl)-1,3-dihydro-2H-1,4-benzodiazepin-2-one (Diastereomer B) following a similar method to that described for Intermediate 6 (step 6) except that methyl iodide was used as the alkylating agent; $\delta_H$ (250 MHz, CDCl$_3$) 8.08 and 7.68 (1H, two d, J=7.6 and 8.0 Hz), 7.54–7.49 (1H, m), 7.34–7.25 (7H, m), 6.30 (1H, m), 5.19–5.07 (4H, m), 3.94 and 3.74 (1H, two m), 3.42 (3H, s), 3.25–3.00 (1H, m), 1.63–1.24 (6H, m), 1.46 and 1.44 (9H, two s), 0.90–0.85 (6H, m); m/z (CI) 549 (M$^+$+1).

2. 3-Amino-5-(1-tert-butyloxycarbonyl-5,5-dimethyl-2,3,4,5,6-hexahydro-1H-azepin- 2-yl)-1,3-dihydro-1-methyl-2H-1,4-benzodiazepin-2-one. Diastereomer B The title compound was prepared from the product of the previous step following a similar method to that described for Intermediate 2; $\delta_H$ (250 MHz, CDCl$_3$) 8.06 and 7.68 (1H, two d), 7.53–7.47 (1H, m), 7.32–7.24 (2H, m), 5.14–4.96 (1H, m), 4.30 (1H, m), 3.95–3.76 (1H, two m), 3.43 and 3.42 (3H, two s), 3.28–3.05 (1H, m), 2.19 (2H, br s), 1.50 and 1.47 (9H, two s), 1.42–1.24 (6H, m), 0.94–0.87 (6H, m); m/z (CI), 415 (M$^+$+1).

INTERMEDIATE 6

3-Amino-5-(1-tert-butyloxycarbonyl-4,4-dimethylpiperidin-2-yl)-1,3-dihydro-1-(1-propyl)-2H-1,4-benzodiazepin-2-one. Diastereomer B 1. 1-tert-butyloxycarbonyl-4,4-dimethylninocolic acid To a stirred solution of 4,4-dimethyl-pipecolic acid (EP 0447704 A1) (24 g) in a mixture of dioxane (380 ml) and 2N sodium hydroxide (112 ml) was added di-tert-butyl dicarbonate (45 g) and the resulting mixture was stirred at room temperature for 23 hours. The dioxane was removed under vacuum and the aqueous residue was diluted with water (50ml), then extracted with diethyl ether (2×60 ml). The ethereal solutions were washed once with water (50 ml) and the combined aqueous solutions were acidified to pH2 with 5N hydrochloric acid, then extracted with ethyl acetate (3×200 ml). The combined organic extracts were washed with brine (2×40 ml), dried (MgSO$_4$) and concentrated to give the title compound (20 g) as a white solid; $\delta_H$ (250 MHz, CDCl$_3$) 4.86–4.55 (1H, m), 3.96–3.78 (1H, m), 3.24–3.05 (1H, m), 2.10–1.96 (1H, m), 1.64 (1H, dd, J=14.0 and 7.4 Hz), 1.54–1.25 (1H, m and s), 0.95 (3H, s), 0.90 (3H, s).

2. 1-tert-Butyloxycarbonyl-2(R,S)-(N,O-dimethylhydroxylamino)carbonyl-4,4-dimethylpiperidine To a stirred solution of 1-tert-butyloxycarbonyl-4,4-dimethylpipecolic acid (24.6 g), N,O-dimethylhydroxylamino hydrochloride (12.12 g) and 1-hydroxybenzotriazole (18.09 g) in anhydrous dimethylformamide (400 ml) was added anhydrous triethylamine (30.7 ml) followed by 1-(3-dimethylaminopropyl)-3-ethylcarbodiimide hydrochloride (21.08 g) and the resulting mixture was stirred at room temperature for 23 hours under a nitrogen atmosphere. Diethyl ether (1 l) was added and the mixture was washed with 1N hydrochloric acid (2×250 ml), 1N sodium hydroxide (1×250 ml), brine (1×200 ml), dried (MgSO$_4$) and concentrated. Flash chromatography (silica gel, hexane-diethyl ether, 40:60) of the residue afforded the title compound (24.1 g) as a white solid; $\delta_H$ (250 MHz, CDCl$_3$) 4.76 (1H, br s), 3.92–3.74 (1H, m), 3.75 (3H, s), 3.58–3.42 (1H, m), 3.19 (3H, s), 1.84 (1H, dd, J=14.0 and 3.3 Hz), 1.64 (1H, dd, J=14.0 and 7.6 Hz), 1.52–1.34 (11H, m and s), 0.94 (3H, s), 0.92 (3H, s); m/z (CI) 301 ($M^+$+1).

3.  [2-(N-tert-Butyloxycarbonylamino)phenyl][2(R,S)-1-tert-butyloxycarbonyl- 4,4-dimethylpiperidin-2-yl]methanone Method A To a cooled (−38° C.) and stirred suspension of N-(tert-butyloxycarbonyl)aniline (5.27 g) in anhydrous diethyl ether (60 ml) was added dropwise, via cannula, tert-butyllithium (1.7M in pentane; 31.3 ml) over 20 minutes, under a nitrogen atmosphere. The resulting clear yellow solution was stirred at −5° C. for 3 hours 15 minutes before it was cooled to −60° C. and a solution of 1-tert-butyloxycarbonyl-2(R,S)-(N,O-dimethylhydroxyl amino)carbonyl-4,4-dimethyl-piperidine (4 g) in anhydrous diethyl ether (15 ml) was added dropwise over 4 minutes. After further 20 minutes, the mixture was allowed to warm to −25° C. and it was stirred for 1 h 50 minutes. Saturated aqueous ammonium chloride (100 ml) was added and the organic phase was decanted off. The aqueous layer was extracted with diethyl ether (1×120 ml) and the combined ethereal phases were washed with 1N hydrochloric acid (1×50 ml), brine (1×50 ml), then dried (MgSO$_4$) and concentrated. The residual oil was triturated with a mixture of hexane and diethyl ether (80:20; 40 ml) and the precipitated N-(tert-butyloxycarbonyl)aniline was removed by filtration. The filtrate was concentrated under vacuum and the residue was purified by flash chromtography (silica gel, hexane-dichloromethane, 50:50 to 30:70) to give the title compound (1.0 g) as a thick yellow oil; $\delta_H$ (250 MHz, CDCl$_3$) 10.18 (1H, br s), 8.38 (1H, d, J=8.4 Hz), 7.75 (1H, d, J=7.9 Hz), 7.50 (1H, t, J=8.2 Hz), 7.03 (1H, t, J=8.0 Hz), 5.46–5.30 (1H, m), 3.94–3.82 (1H, m), 3.54–3.40 (1H, m), 1.79 (1H, d, J=6.4 Hz), 1.60–1.22 (20H, m), 0.92 (3H, s), 0.78 (3H, s); m/z (CI), 432 ($M^-$).

Method B a. 1-tert-Butyloxycarbonyl-4,4-dimethylpiperidino-2(R,S)-carboxaldehyde To a cooled (−75° C.) and stirred solution of 1-tert-butyloxycarbonyl- 2(R,S)-(N,O-dimethylhydroxylamino)carbonyl-4,4-dimethylpiperidine (4.0 g) in anhydrous toluene (200 ml) was added dropwise, via cannula, diisobutylaluminium hydride (1M in toluene; 21.3 ml) over 45 minutes, under nitrogen. The mixture was stirred at −75° C. for 3.5 hours and at −30° C. for 3.5 hours before more diisobutylaluminium hydride (4 ml) was added. After further 1 hour of stirring at −30° C., the excess diisobutylaluminium hydride was destroyed by addition of methanol (14 ml) (CAUTION! hydrogen evolution) followed by 10% aqueous citric acid (140 ml). Products were extracted with diethyl ether (3×125 ml) and the combined organic solutions were washed with brine (2×50 ml), then dried (MgSO$_4$) and concentrated. Flash chromatography of the residue (silica gel, hexane-diethyl ether, 60:40) afforded the title compound (2.0 g) as a colourless oil; $\delta_H$ (250 MHz, CDCl$_3$) 9.55 (1H, s), 4.26 (1H, t, J=5.7 Hz), 3.80–3.51 (1H, m), 3.30–3.14 (1H, m), 1.80 (1H, dd, J=13.8 and 5.1 Hz), 1.57 (1H, dd, J=13.8 and 6.5 Hz), 1.52–1.30 (11H, m and s), 0.98 (3H, s), 0.85 (3H, s); m/z (CI) 242 ($M^+$+1).

b [2-(N-tert-Butyloxycarbonylamino)phenyl][1-tert-butyloxycarbonyl-4,4-dimethylpiperidin-2-yl]methanol To a cooled (−75° C.) and stirred solution of N-(tert-butyloxycarbonyl)aniline (362 g) in anhydrous tetrahydrofuran (30 ml) was added dropwise, via cannula, tert-butyllithium (1.7M in pentane; 21.5 ml) over 27 minutes, under a nitrogen atmosphere. After further 10 minutes at −75° C., the mixture was allowed to warm to −22° C. and it was stirred for 2 hours before it was re-cooled to −70° C. A solution of the aldehyde from the previous step (1.95 g) in anhydrous tetrahydrofuran (15 ml) was added over 9 minutes and the resulting solution was stirred at −75° C. for 1 h 50 minutes and at −30° C. for 50 minutes. Water (60 ml) was added and products were extracted with ethyl acetate (2×80 ml), then dried (MgSO$_4$) and concentrated. Flash chromatography of the residual oil (silica gel, hexane-diethyl ether, 60:40) gave 1.57 g of the title compound (single diastereomer); $\delta_H$ (250 MHz, CDCl$_3$) 8.19 (1H, s), 7.95 (1H, d, J=7.8 Hz), 7.32–7.24 (1H, m), 7.14–7.06 (1H, m), 7.04–6.94 (1H, m), 4.84 (1H, d, J=9.1 Hz), 4.40–4.28 (1H, br, q), 3.80–3.62 (1H, m,), 3.25–3.06 (1H, m), 1.51 (9H, s), 1.50–0.98 (4H, m), 0.91 (3H, s), 0.83 (3H, s); m/z (CI), 435 ($M^+$+1).

c.  [2-(N-tert-Butyloxycarbonylamino)phenyl][2(R,S)-1-tert-butyloxycarbonyl- 4,4-dimethylpiperidin-2-yl]methanone To a stirred solution of the preceding alcohol (1.50 g) and 4-methylmorpholine-N-oxide monohydrate (850 mg) in anhydrous dichloromethane (35 ml) was added 4 A molecular sieves (1.6 g) and the mixture was stirred for 15 minutes before tetrapropylnmmonium perruthenate (60 mg) was added. The resulting mixture was stirred at room temperature for 19 hours, diluted with dichloromethane (200 ml) and washed with 10% aqueous sodium bicarbonate (1×60 ml), brine (1×60 ml) and saturated aqueous copper (II) sulphate (60 ml). The organic solution was then filtered through a plug of silica gel and eluted with diethyl ether (3×40 ml). The filtrate was concentrated under vacuum and the remaining residue was purified by flash chromatography (silica gel, hexane-diethyl ether, 80:20) to give the title compound (1.16 g) as a thick colourless oil.

4.  [2-Aminophenyl][2(R,S)-1-tert-butyloxycarbonyl-4,4-dimethylpiperidin-2-yl]methanone A solution of [2-(N-tert-butyloxycarbonylamino) phenyl][2(R,S)-1-tert-butyloxycarbonyl-4,4-dimethylpiperidin-2-yl]methanone(2.49 g) in a mixture of anhydrous dichloromethane (40 ml) and trifluoroacetic acid (12 ml) was stirred at room temperature for 30 minutes, under nitrogen. Solvents were removed under vacuum and the residue azeotroped with methanol (1×50 ml). The remaining oil was dissolved in a mixture of dichloromethane and ethyl acetate (1:1, 100 ml) and washed with saturated aqueous potassium carbonate (40 ml). The aqueous phase was extracted with the same solvent mixture (1×100 ml) and the combined organic solutions were washed with brine (1×40 ml), then dried (Na$_2$SO$_4$) and concentrated. The remaining yellow oil was dissolved in a mixture of anhydrous tetrahydrofuran (20 ml) and anhydrous dichloromethane (20 ml) and anhydrous triethylamino (800 μl) was added Di-tert-butyl dicarbonate (1.5 g) was added and the mixture was stirred at room temperature for 15 hours, under nitrogen. The reaction mixture was partitioned between 1N hydrochloric acid (40 ml) and diethyl ether (2×150 ml) and the combined organic phases were washed with brine (2×30 ml), dried (MgSO$_4$) and concentrated. Flash chromatography of the residue (silica gel, hexane-diethyl ether, 60:40) gave the title compound (1.72 g) as a white solid; mp 128°–130° C. (hexane-diethyl ether); $\delta_H$ (360 MHz, CDCl$_3$), 7.65 (1H, d, J=8.0 Hz), 7.29–7.24 (1H, m), 6.72 (1H, d, J=7.6 Hz), 6.67 (1H, t, J=8.0 Hz), 5.48–5.23 (1H, m), 3.92–3.82 (1H, m), 3.56–3.44 (1H, m), 1.92–1.78 (2H, m), 0.93 (3H, s), 0.80 (3H, s); m/z (CI) 333 ($M^+$+1).

5.  3-(Benzyloxycarbonylamino)-5-(1-tert-butyloxycarbonyl-4,4-dimethylpiperidin-2-yl)-1,3-dihydro-2H-1,4-benzodiazepin-2-one. Diastereomers A and B The title compounds were prepared from [2-aminophenyl][2(R,S)-1-tert-butyloxycarbonyl-4,4-dimethylpiperidin-2-yl]methanone (1.7 g) following a similar method to that described for Intermediate 1 (step 4). The crude product was purified by flash chromatography (silica gel, hexane-ethyl acetate, 60:40) to give the title compound (Diastereomer A. less polar: 100 mg) and the title compound (Diastereomer B. more polar: 1.0 g) as white foams.

DIASTEREOMER B:

$\delta_H$ (250MHz, DMSO-d$_6$)10.75 (1H, s), 8.27–8.14 (1H, br d), 7.74–7.62 (1H, br d), 7.58 (1H, t, J=7.2 Hz), 7.38–7.16 (7H, m), 5.46–5.26 (1H, m), 5.04–4.86 (3H, m), 3.80–3.66 (1H, m), 1.64–1.08 (13H, m), 0.74 (3H, s), 0.53 (3H, s); m/z (CI) 521 (M$^+$+1).

6. 3-(Benzyloxycarbonylamino)-5-(1-tert-butyloxycarbonyl-4,4-dimethylpiperidin-2-yl)-1.3-dihydro-1-(1-propyl)-2H-1,4-benzodiazepin-2-one. Diastereomer B To a stirred mixture of 3-(benzyloxycarbonylamino)-5-(1-tert-butyloxycarbonyl- 4,4-dimethylpiperidin-2-yl)-1,3-dihydro-2H-1,4-benzodiazepin-2-one (Diastereomer B) (200 mg) and cesium carbonate (132 mg) in anhydrous dimethylformamide (6 ml) was added 1-iodopropane (56 μl) and the mixture was stirred at room temperature for 1 hour 40 minutes, under a nitrogen atmosphere. Water (25 ml) was added and the product was extracted with ethyl acetate (2×50 ml), then washed with brine (1×20 ml), dried (MgSO$_4$) and concentrated. Flash chromatography of the residue (silica gel, hexane-ethyl acetate, 70:30) gave the title compound (200 mg) as a thick colourless oil; $\delta_H$ (360 MHz, DMSO-d$_6$) 8.19 (1H, br d, J=6.3 Hz), 7.76–7.56 (3H, m), 7.42–7.29 (6H, m), 5.40–5.30 (1H, m), 5.02–4.92 (3H, m), 3.80–3.68 (2H, m), 3.64–3.54 (1H, m), 3.28–3.10 (1H, m), 1.80–1.54 (3H, m), 1.40–1.20 (12H, m), 0.88 (3H, t, J=7.3 Hz), 0.78 (3H, s), 0.56 (3H, s); m/z (CI) 563 (M$^+$+1).

7. 3-Amino-5-(1-tert-butyloxycarbonyl-4,4-dimethylpiperidin-2-yl)-1,3-dihydro-1-(1-propyl)-2H-1,4-benzodiazepin-2-one. Diastereomer B The title compound was prepared from 3-(benzyloxycarbonyl-amino)- 5-(1-tert-butyloxycarbonyl-4,4dimethylpiperidin-2-yl)-1,3-dihydro- 1-(1-propyl)-2H-1,4-benzodiazepin- 2-one (Diastereomer B) using a similar method to that described for Intermediate 2; colourless thick oil; $\delta_H$ (250 MHz, CDCl$_3$), 7.64–7.46 (2H, m), 7.36 (1H, d, J=7.7 Hz), 7.24 (1H, t, J=7.4 Hz), 5.44–5.32 (1H, m), 4.34 (1H, s), 3.96–3.80 (2H, m), 3.52–3.24 (2H, m), 2.36–1.90 (3H, m), 1.80–1.24 (14H, m), 0.97 (3H, t, J=7.4 Hz), 0.80 (3H, s), 0.59 (3H, s); m/z (CI), 429 (M$^+$+1).

EXAMPLE 4

N-[2,3-Dihydro-5-(5,5-dimethyl-2,3,4,5,6-hexahydro-1H-azepin- 2-yl)-2-oxo-1-(1-propyl)-1H-1,4-benzodiazepin-3-yl]-N'-[3-methylphenyl]urea hydrochloride. Diastereomer B The title compound free base was prepared from Intermediate 4 using a similar method to that described for Example 1 (steps 1 and 2); the hydrochloride salt was prepared; mp 174°–184° C. (dec); $\delta_H$ (360 MHz, DMSO-d$_6$), 9.33 (1H, br s), 9.27 (1H, s), 8.52 (1H, br s), 7.92 (1H, d, J=7.6 Hz), 7.76–7.74 (2H, m), 7.52–7.46 (2H, m), 7.20–7.15 (2H, m), 7.09 (1H, t, J=7.7 Hz), 6.73 (1H, d, J=7.5 Hz), 5.21 (1H, d, J=8.3 Hz), 4.95 (1H, m), 4.22 (1H, m), 3.73 (1H, m), 3.18 (2H, m), 2.22 (3H, s), 1.73–1.23 (8H, m), 0.92 (3H, s), 0.76 (3H, t, J=7.3 Hz); m/z (CI), 476 (M$^+$+1). (Found: C, 63.84; H, 7.28; N, 13.14. C$_{28}$H$_{37}$N$_5$O$_2$×1.0HCl×0.7H$_2$O requires: C, 64.09; H, 7.57; N, 13.35%).

EXAMPLE 5

N-[2,3-Dihydro-5-(2,3,4,5,6-hexahydro-1,5,5,-trimethyl-1H-azepin-2-yl)-2-oxo-1-(1-propyl)-1H-1,4-benzodiazepin-3-yl]-N'-[3-methylphenyl]urea hydrochloride. Diastereomer B The title compound free base was prepared from the product of Example 4, following a similar method to that described for Example 3; the hydrochloride salt was prepared; mp 160°–167° C; $\delta_H$ (360 MHz, DMSO-d$_6$) 9.33 (1H, s), 9.15 (1H, br m), 7.97 (1H, d, J=7.6 Hz), 7.82–7.73 (2H, m), 7.56–7.49 (2H, m), 7.19–7.15 (1H, m), 7.09 (1H, t, J=7.7 Hz), 6.73 (1H, d, J=7.2 Hz), 5.13 (1H, d, J=7.5 Hz), 5.03 (1H, m), 4.18 (1H, m), 3.75 (1H, m), 3.40 (2H, m), 2.98 and 2.97 (3H, two s), 2.22 (3H, s), 1.76–1.24 (8H, m), 0.92 (3H, s), 0.83 (3H, s), 0.78 (3H, t, J=7.3 Hz); m/z (CI) 490 (M$^+$+1). (Found: C, 62.41; H, 7.77; N-12.41. C$_{29}$H$_{39}$N$_5$O$_2$×1.0HCl×1.8H$_2$O requires: C, 62.36; H, 7.87; N, 12.54%).

EXAMPLE 6

N-[2,3-Dihydro-5-(5,5-dimethyl-2,3,4,5,6-hexahydro-1H-azepin-2-yl)-1-methyl-2-oxo-1H-1,4-benzodiazepin-3-yl]-N'-[3-methylphenyl]urea hydrochloride. Diastereomer B The title compound free base was prepared from Intermediate 5 following a similar method to that described for Example 1 (steps 1 and 2); the hydrochloride salt was prepared; mp 193°–203° C; $\delta_H$ (360 MHz, DMSO-d$_6$) 9.40 (1H, br m), 9.27 (1H, s), 8.49 (1H, br m), 7.92 (1H, dd), 7.77 (1H, dt), 7.65 (1H, dd), 7.48 (2H, m), 7.19–7.15 (2H, m), 7.09 (1H, t, J=7.6 Hz), 6.73 (1H, dd), 5.24 (1H, d, J=8.2 Hz), 4.94 (1H, m), 3.37 (3H, s), 3.18 (2H, m), 2.22 (3H, s), 1.74–1.24 (6H, m), 0.91 (3H, s), 0.83 (3H, s); m/z (FAB), 448 (M$^+$+1). (Found: C, 63.57; H, 7.22; N, 13.98. C$_{26}$H$_{33}$N$_5$O$_2$×1.0 HCl×0.4H$_2$O requires: C, 63.57; H, 7.14; N, 14.26%).

EXAMPLE 7

N-[2,3-Dihydro-5-(5,5-dimethyl-2,3,4,5,6-hexahydro-1H-azepin- 2-yl)-1-methyl-2-oxo-1H-1,4-benzodiazepin-3-yl]-N'-[5-indanyl]urea hydrochloride. Diastereomer B The title compound free base was prepared from Intermediate 5 following a similar procedure to that described for example 1 (steps 1 and 2) except that 5-indanyl isocyanate was used instead of m-tolyl isocyanate; the hydrochloride salt was prepared; mp 171°–175° C. (dec); $\delta_H$ (360 MHz, DMSO-d$_6$) 9.41 (1H, m), 9.17 (1H, s), 8.47 (1H, m), 7.91 (1H, d, J=7.9 Hz), 7.76 (1H, t, J=7.8 Hz), 7.65 (1H, d, J=8.1 Hz), 7.48 (1H, t, J=7.6 Hz), 7.43 (1H, d, J=8.5 Hz), 7.26 (1H, s), 7.07 (2H, m), 5.25 (1H, d, J=8.4 Hz), 4.93 (1H, m), 3.37 (3H, s), 3.18 (2H, m), 2.76 (4H, q, J=6.9 Hz), 1.96 (2H, qn, J=7.3 Hz), 1.70–1.24 (6H, m), 0.91 (3H, s), 0.83 (3H, s); m/z (CI), 473 (M$^-$). (Found: C, 64.50; H, 7.13; N, 13.09. C$_{28}$H$_{35}$N$_5$O$_2$×1.0HCl×0.6 H$_2$O requires: C, 64.56; H, 7.20; N, 13.45% ).

EXAMPLE 8

N-[2,3-Dihydro-5-(4,4-dimethylpiperidin-2-yl)-2-oxo-1-(1-propyl)-1H-1,4-benzodiazepin-3-yl]-N'-[3-methylphenyl] urea hydrochloride. Diastereomer B 1. N-[5-(1-tert-Butyloxycarbopyl-4,4-dimethylpiperidin-2-yl)-2,3-dihydro-2-oxo-1-(1-propyl)-1H, 1,4-benzodiazepin-3-yl]-N'-[3-methylphenyl]urea. Diastereomer B The title compound was prepared in 91% yield from Intermediate 6 following a similar method to that described for Example 1 (step 1); white solid; mp 201°–205° C. (hexane-diethyl ether); $\delta_H$ (360 MHz, DMSO-d$_6$) 8.83 (1H, s), 7.78–7.65 (2H, m), 7.60 (1H, d, J=8.0 Hz), 7.40 (1H, t, J=7.2 Hz), 7.18 (1H, d, J=8.8 Hz), 7.15–7.04 (3H, m), 6.71 (1H, d, J=6.6 Hz), 5.36 (1H, br s), 5.10 (1H, br s), 3.82–3.70

(2H, m), 3.60–3.48 (1H, m), 3.20–3.00 (1H, m), 2.22 (3H, s), 1.84–1.54 (3H, m), 1.40–1.20 (12H, m), 0.90 (3H, t, J=7.3 Hz), 0.78 (3H, s), 0.55 (3H, s); m/z (CI) 562 (M$^-$+1).

2. N-[2,3-Dihydro-5-(4,4-dimethylpiperidin-2-yl)-2-oxo-1-(1-propyl)-1H, 1,4-benzodiazepin-3-yl]-N'-[3-methylphenyl]urea hydrochloride. Diastereomer B The title compound free base was prepared from the product of the previous step following a similar method to that described for Example 1 (step 2); the hydrochloride salt was prepared and recrystallised from methanol-diethyl ether; mp 181°–183° C. (dec.); $\delta_H$ (360 MHz, CDCl$_3$) 10.63 (1H, s), 9.10 (1H, br d), 9.02 (1H, d, J=8.6 Hz), 8.62 (1H, br q), 7.83 (1H, dd, J=7.9 and 1.2 Hz), 7.55 (1H, dt, J=7.1 and 1.3 Hz), 7.38–7.24 (4H, m), 6.99 (1H, t, J=7.7 Hz), 6.69 (1H, d, J=7.5 Hz), 5.42 (1H, d, J=8.6 Hz), 4.35–4.21 (2H, m), 3.54–3.43 (1H, m), 3.15–2.93 (2H, m), 2.25 (3H, s), 1.62–1.50 (1H, m), 1.32–1.04 (3H, m), 0.95–0.86 (4H, m and s), 0.73 (3H, t, J=7.3 Hz), 0.64 (3H, s), 0.44 (1H, t, J=13.3 Hz); m/z (CI) 461 (M$^-$). (Found: C, 64.65; H, 7.21; N, 13.87. C$_{27}$H$_{35}$N$_5$O$_2$×1.0 HCl×0.2 H$_2$O requires: C, 64.64; H, 7.31; N, 13.96%).

The enantiomers of this compound were separated by HPLC using a DNBL column (250×20 mm id.; 5 μm particle size) and eluting with hexane-ethanol (70:30; flow 20 ml/min; detection at 230 nm) to afford ENANTIOMER A (retention time 16.1 minutes) and ENANTIOMER B (retention time 23.5 minutes). The e-n-antiomeric purity of both enantiomers was shown to be >99% e.e. for Enantiomer A and 97.7% e.e. for Enantiomer B, using an analytical DNBL column (250×4.6 mm id; 5 μm particle size) and eluting with a mixture of methanol, 1-chlorobutane and acetic acid (10:89:1) (retention times 4.9 and 6.8 minutes respectively).

EXAMPLE 9

N-[2,3-Dihydro-1-(2-methylpropyl)-2-oxo-5-(piperidin-4-yl)-1H-1,4-benzodiazepin-3-yl]-N'-[3-methylphenyl]urea trifluoroacetic acid salt 1. 4-(1H-Indol-3-yl)-1-tert-butyloxycarbonyl-3,4-dehydropiperidine A mixture of indole (19.6 g, 0.17 mol), 1-tert-butyloxycarbopyl- 4-piperidone (23.3 g, 0.11 mol) and methanolic potassium hydroxide (300 ml of a 2M solution) was heated at reflux for 18 h. On cooling to room temperature a solid precipitated out which was collected by filtration. This solid was partitioned between dichloromethane (300 ml) and water (300 ml). The organic layer was separated, dried (Na$_2$SO$_4$) and evaporated in vacuo to afford the title compound (25.5 g, 77%) as a white solid.

The filtrate, from above, was chromatographed on silica gel using petrol-ethyl acetate (3:1) as the eluant, to afford more of the desired product (3.8 g, 12%) as a white solid; $\delta_H$ (360 MHz, CDCl$_3$) 1.50 (9H, s), 2.56 (2H, m), 3.68 (2H, t, J=5.7 Hz), 4.13 (2H, m), 6.16 (1H, m), 7.13–7.25 (3H, m), 7.37 (1H, d, J=7.8 Hz), 7.87 (1H, d, J=7.8 Hz), 8.19 (1H, br s); m/z (EI) 298 (M$^+$).

2. 4-(1H-Indol-3-yl)-1-tert-butyloxycarbonylpiperidine 4-(1H-Indol-3-yl)-1-tert-butyloxycarbonyl-3,4-dehydropiperidine (4.5 g, 0.015 mol) was dissolved in ethanol (250 ml), containing 10% palladium on carbon (0.5 g, 11% (w/w)), and hydrogenated at 44 psi for 1 h. After this time the catalyst was filtered off, the solvent evaporated in vacuo and the residue chromatographed on silica gel using petrol-ethyl acetate (3:1) as the eluant. The desired product (3.5 g, 78%) was isolated as a white solid; $\delta_H$ (360 MHz, CDCl$_3$) 1.50 (9H, s), 1.61–1.72 (2H, m), 2.03 (2H, m), 2.86–3.01 (3H, m), 4.23 (2H, m), 6.95 (1H, d, J=2 Hz), 7.08 (1H, dd, J=7 and 7 Hz), 7.17 (1H, dd, J=7 and 7 Hz), 7.35 (1H, d, J=7.3 Hz), 7.62 (1H, d, J=7.9 Hz), 7.97 (1H, br s); m/z (EI) 300 (M$^+$).

3. (1-tert-Butyloxycarbonylpiperidin-4-yl)(2-formylaminophenyl)methanone

Ozone was bubbled through a solution of 4-(1H-indol-3-yl)- 1-tert-butyloxycarbonylpiperidine (15.3 g, 0.05 mol) in dichloromethane (500 ml) at −78° C. for 40 min. After this time oxygen was bubbled through the mixture for 10 min then dimethyl sulphide (22 ml, 0.3 mol) was added dropwise and the solution allowed to attain room temperature and stirred overnight. The solvent was evaporated in vacuo and the residue chromatographed on silica gel, using 2:1 petrol-ethyl acetate as the eluant, to afford the title compound (12.2 g, 73%) as a yellow oil; $\delta_H$ (360 MHz, CDCl$_3$) 1.50 (9H, s), 1.58–1.76 (2H, m), 1.84 (2H, m), 2.87 (2H, m), 3.46 (1H, m), 4.18 (2H, m), 7.18 (1H, dd, J=7.6 and 7.5 Hz), 7.57 (1H, dd, J=7.8 and 7.7 Hz), 7.91 (1H, d, J=8.0 Hz), 8.48 (1H, br s), 8.75 (1H, d, J=8 Hz), 11.49 (1H, br s); m/z (EI) 332 (M$^+$).

4. (1-tert-Butyloxygarbonylpiperidin-4-yl)(2-aminophenyl)methanone

The product from the previous step (2.3 g, 6.9 mmol) was dissolved in a solution of 2M potassium hydroxide in methanol (120 ml) and was heated at reflux for 1 h. After this time the reaction mixture was cooled to room temperature and the solvent removed in vacuo. The residue was partitioned between dichloromethane (100 ml) and water (100 ml). The organic layer was separated and the aqueous phase washed with more dichloromethane (100 ml). The combined organic layers were washed with brine (100 ml), the organic phase separated, dried (MgSO$_4$) and evaporated in vacuo. The residue was then chromatographed on silica gel, using petrol-ethyl acetate (3:1) to afford a colourless oil. The oil was then taken up in diethyl ether (50 ml) and evaporated to afford the title compound (1.45 g, 69%) as a white solid; $\delta_H$ (360 MHz, CDCl$_3$) 1.48 (9H, s), 1.64–1.80 (4H, m), 2.87 (2H, m), 3.41 (2H, m), 4.17 (2H, m), 6.28 (2H, br s), 6.63–6.69 (2H, m), 7.28 (1H, dd, J=7 and 7 Hz), 7.73 (1H, d, J=9 Hz); m/z (EI) 304 (M$^+$).

5. 5-(1-tert-Butyloxygarbonylpiperidin-4-yl)-1,3-dihydro-3(R,S)-[(benzyloxygarbonyl)amino]- 2H, 1,4-benzodiazepin-2-one α-(Isopropylthio)-N-(benzyloxygarbonyl)glycine (1.42 g, 5.0 mmol) was dissolved in dichloromethone (55 ml) and cooled to 0° C. The stirred solution was then treated with n-methyl morpholine (0.55 ml, 5.0 mmol) followed by isobutyl chloroformate (0.65 ml, 5.0 mmol). The resulting reaction mixture was stirred for a further 15 min at 0° C., then heated to reflux. The reflux/rig reaction mixture was treated dropwise, over 20 min, with a solution of (1-tert-butyloxycarbonylpiperidin-4-yl)(2-aminophenyl)methanone (1.45 g, 4.77 mmol) in dichloromethane (7 ml). After addition was complete the reaction was heated at reflux for a further 4 h. The mixture was then washed in succession with 10% citric acid solution (2×25 ml), saturated sodium bicarbonate solution (2×25 ml) and brine (25 ml). The dried (MgSO$_4$) organic phase was evaporated to afford the crude product as a pale orange solid, which was used without further purification.

The crude (isopropylthio)glycinamide was dissolved in anhydrous tetrahydrofuran (40 ml) and cooled to 0° C. Ammonia gas was bubbled through the stirred solution for 30 min before adding mercuric chloride (1.42 g, 5.3 mmol) inone portion. Ammonia was continually bubbled through the solution for a further 5 hours, then the suspended solids were filtered off. The solvent was evaporated in vacuo to leave an oil, which was used without further purification.

The crude α-aminoglycinamide was dissolved in glacial acetic acid (40 ml) and the resulting reaction mixture was stirred at room temperature overnight, before removing the solvent in vacuo. The residue was partitioned between ethyl acetate (100 ml) and 1N sodium hydroxide solution (100 ml). The organic phase was separated, dried (MgSO$_4$) and evaporated. The residue was chromatographed on silica gel, using 1:1 petrol-ethyl acetate as the eluant, to afford the title compound (1.66 g, 71%); δ$_H$ (360 MHz, CDCl$_3$) 1.43 (9H, s), 1.63 (2H, m), 1.81–1.95 (2H, m), 2.72–2.93 (2H, m), 3.84–4.18 (2H, m), 5.11 (2H, m), 5.18 (1H, d, J=8.2 Hz), 6.41 (1H, d, J=7.8 Hz), 7.07 (1H, d, J=8.0 Hz), 7.25–7.37 (6H, m), 7.48 (1H, dd, J=7 and 7 Hz), 7.58 (1H, d, J=7.8 Hz), 8.22 (1H, br s); m/z (FAB), 493 (M$^+$+1).

6. 5, (1-tert-Butyloxycarbonylpiperidin-4-yl)-1,3-dihydro-1-(2-methylpropyl)- 3(R,S)-3-[(benzyloxycarbonyl)amino]-2H-1,4-benzodiazepin-2-one To a solution of 5-(1-tert-Butyloxycarbonylpiperidin-4-yl)-1,3-dihydro- 3(R,S)-[(benzyloxycarbonyl)amino]-2H-1,4-benzodiazepin- 2-one (2.0 g, 4.07 mmol) in anhydrous dimethylformamide (15 ml) at 0° C., under nitrogen, was added sodium hydride (163 mg of a 60% dispersion in mineral oil, 4.07 mmol). The suspension was stirred at 0° C. for 30 min then 2-methylpropyl iodide (0.51 ml, 4.47 mmol) was added dropwise. The mixture was stirred at 0° C. for 1 h then the solution was allowed to attain room temperature and stirred, under nitrogen, for a further 20 h. After this time more 2-methylpropyl iodide (0.23 ml, 2.03 mmol) was added and the solution stirred for a further 5 h. The solvent was evaporated in vacuo and the residue partitioned between ethyl acetate (4×25 ml) and water (25 ml). The combined organic layers were washed with brine (50 ml), dried (MgSO$_4$) and evaporated. The residue was chromatographed on silica gel using 35% ethyl acetate in petrol followed by 1:1 petrol-ethyl acetate. The desired product (1.45 g, 65%) was isolated as a pale yellow solid; δ$_H$ (360 MHz, CDCl$_3$) 0.72 (3H, d, J=6.6 Hz); 0.79 (3H, d, J=6.7 Hz), 1.25–1.33 (1H, m), 1.44 (9H, s), 1.54–1.66 (2H, m), 1.72–1.84 (1H, m), 1.98–2.06 (1H, m), 2.67–2.84 (2H, m), 2.90–3.00 (1H, m), 3.42 (1H, dd, J=13.1 and 5.1 Hz), 4.06–4.32 (3H, m), 5.05–5.14 (3H, m), 6.55 (1H, d, J=8.1 Hz), 7.25–7.38 (7H, m), 7.50 (1H, t, J=7.3 Hz), 7.55 (1H, d, J=7.5 Hz); m/z (CI, NH$_3$) 549 (M$^+$+1).

7. 3 (R,S)-Amino-5-(1-tert-butyloxycarbonylpiperidin-4.-yl)-1,3-dihydro-1-(2-methylpropyl)-2H-1,4-benzodiazepin-2-one A solution of 5-(1-tert-butyloxycarbonylpiperidin-4-yl)-1,3-dihydro-1-( 2-methylpropyl)-3(R,S)-[(benzyloxycarbonyl)amino]-2H-1,4-benzodiazepin-2-one (1.4 g, 2.55 mmol) in methanol (96 ml) and formic acid (4 ml) was added dropwise to a stirred suspension of 10% palladium on carbon (250 mg, 18% (w/w)) in methanol (14 ml) and formic acid (1 ml), under nitrogen. The mixture was stirred for 1 h at room temperature then more palladium on carbon (250 mg, 18% (w/w)) was added (as a slurry in water). After stirring for a further 30 min the catalyst was filtered off and washed with acetone. The filtrate was evaporated to give a pale yellow oil, which was partitioned between 10% sodium carbonate solution (50 ml) and ethyl acetate (2×50 ml). The combined organic extracts were dried (Na$_2$SO$_4$) and evaporated in vacuo to afford the desired product (0.95 g, 90%) as yellow solid; δ$_H$ (360 MHz, CDCl$_3$) 0.72 (3H, d, J=6.6 Hz), 0.79 (3H, d, J=6.7 Hz), 1.27–1.39 (1H, m), 1.45 (9H, s), 1.52–1.66 (2H, m), 1.76–1.89 (1H, m), 1.95–2.04 (1H, m), 2.66–2.84 (2H, m), 2.84–3.00 (1H, m), 3.42 (1H, dd, J=14.3 and 5.3 Hz), 4.04–4.16 (1H, m), 4.16–4.26 (2H, m), 4.28 (l/1, s), 4.32 (1H, dd, J=13.8 and 9.1 Hz), 7.25 (1H, t, J=7.5 Hz), 7.35 (1H, d, J=7.5 Hz), 7.47–7.54 (2H, m); m/z (EI), 414 (M$^+$).

8. N-[5-(1-tert-Butyloxycarbonylpiperidin-4-yl)-2,3-dihydro-1-( 2-methylpropyl)-2-oxo-1H-1,4-benzodiazepin-3-yl] -N'-[3-methylphenyl]urea To a solution of the previous amino (0.35 g, 0.85 mmol) [Step 7] in anhydrous tetrahydrofuran (5 ml) was added 3-methylphenyl isocyanate (110 μl, 0.85 mmol) dropwise, under nitrogen. The resultant suspension was left to stand at room temperature for 1 h, after which time ether (20 ml) was added The solid was filtered off, washed with more ether and recrystallized from methanol to afford the title urea (290 mg, 62%) as a white solid. The mother liquors were evaporated and the residue chromatographed on silica gel, using 3:1 petrol-ethyl acetate followed by 1:1 petrol-ethyl acetate as the eluant. The product (103 mg, 22%) was isolated as a white solid; mp 202°–204° C. (MeOH); δ$_H$ (360 MHz, CDCl$_3$) 0.71 (3H, d, J=6.6 Hz), 0.78 (3H, d, J=6.6 Hz), 1.25–1.31 (1H, m), 1.43 (9H, s), 1.58–1.64 (2H, m), 1.73–1.77 (1H, m), 1.98–2.04 (1H, m), 2.31 (3H, m), 2.68–2.80 (2H, m), 2.91–2.98 (1H, m), 3.43 (1H, dd, J=13.8 and 5.1 Hz), 4.04–4.24 (2H, m), 4.29 (1H, dd, J=13.8 and 9.2 Hz), 5.33 (1H, d, J=6.5 Hz), 6.63 (1H, d, J=7.8 Hz), 6.70 (1H, s), 6.87 (1H, d, J=7.3 Hz), 7.08 (1H, d, J=8.1 Hz), 7.17 (1H, t, J=7.7 Hz), 7.20 (1H, s), 7.28 (1H, d, J=7.9 Hz), 7.36 (1H, d, J=8.0 Hz), 7.51 (1H, t, J=7.1 Hz), 7.56 (1H, d, J=7.9 Hz); m/z (CI, NH$_3$) 547 (M$^+$).

9. N-[2,3-Dihydro-1-(2-methylpropyl)-2-oxo-5-(piperidin-4-yl)-1H, 1,4-benzodiazepin-3-yl]-N'-[3-methylphenyl]urea trifluoroacetic acid salt To a solution of N-[5-(1-tert-butyloxycarbonylpiperidin-4-yl)-2,3-dihydro- 1-(2-methylpropyl)-2-oxo-1H-1,4-benzodiazepin-3-yl]-N'-[3-methylphenyl]urea (350 mg, 0.64 mmol) in anhydrous dichloromethane (20 ml) was added trifluoroacetic acid (2.5 ml) dropwise, under an atmosphere of nitrogen. The solution was stirred at room temperature for 1.5 h then the solvent was evaporated in vacuo and the resultant yellow gum triturated and azeotroped with toluene (10 ml). The residue was then triturated with toluene (10 ml) and finally crystallised from methanol to afford the title compound (86 mg, 24%) as a white solid. Evaporation of the mother liquors afforded additional amounts of the title compound (244 mg, 68%) also as a white solid; mp 228°–230° C. (MeOH); δ$_H$ (360 MHz, DMSO-d$_6$)0.63 (3H, d, J=6.6 Hz), 0.76 (3H, d, J=6.7 Hz), 1.37–1.49 (2H, m), 1.64–1.68 (1H, m), 1.76–1.86 (1H, m), 2.06–2.12 (1H, m), 2.22 (3H, s), 2.92–2.99 (2H, m), 3.22–3.37 (3H, m), 3.62 (1H, dd, J=13.9 and 4.5 Hz), 4.15 (1H, dd, J=13.9 and 8.9 Hz), 5.05 (1H, d, J=7.9 Hz), 6.72 (1H, d, J=6.5 Hz), 7.06–7.12 (2H, m), 7.18 (1H, s), 7.33 (1H, d, J=8.4 Hz), 7.42 (1H, t, J=6.7 Hz), 7.64–7.72 (2H, m), 7.80 (1H, d, J=6.9 Hz), 8.38 (1H, br s), 8.92 (1H, br s).

EXAMPLE 10

N-[2,3-Dihydro-5-(N-methylpiperidin-4-yl)-1-(2-methylpropyl)-2-oxo-1H-1,4-benzodiazepin-3-yl]-N'-[3-methylphenyl]urea hydrochloric acid salt N-[2,3-Dihydro-1-(2-methylpropyl)-2-oxo-5-(piperidin-4-yl)- 1H-1,4-benzodiazepin-3-yl]-N'-[3-methylphenyl]urea trifluoroacetic acid salt (200 mg, 0.356 mmol) was partitioned between dichloromethane (10 ml) and saturated potassium carbonate solution (10 ml). The organic phase was separated and the aqueous phase washed with dichloromethane (2×10 ml). The combined organic layers were dried (MgSO$_4$) and evaporated in vacuo to give the free base (153 g, 0.34 mmol).

The free base (153 mg, 0.34 mmol) was dissolved in methanol (10 ml), to which was added sodium cyanoborohydride (43 g, 0.68 mmol) and acetic acid (87 µl, 1.54 mmol). An aqueous solution of formaldehyde (69 µl of a 37% w/v solution, 0.86 mmol) was then added dropwise, and the reaction mixture stirred for 1.5 h under an atmosphere of nitrogen. The solvent was then evaporated and the residue partitioned between ethyl acetate (3×10 ml) and saturated potassium carbonate solution (10 ml). The combined layers were dried (MgSO$_4$) and evaporated in vacuo. The residue was chromatographed on silica gel rising dichloromethane-methanol-aqueous ammonia (90:10:1) as the eluant, to afford the N-methylated derivative (143 mg, 91%) as a white solid.

This solid was dissolved in dichloromethane (15 ml) and ethereal hydrogen chloride (2 ml) was added. The solution was diluted with ether (20 ml) and the solvents evaporated in vacuo to afford a yellow solid The yellow solid was recrystallized from methanol/ether to afford the title compound (100 mg, 70%) as a white solid; mp 190° C. (dec.); $\delta_H$ (360 MHz, D$_2$O) 0.67 (3H, d, J=6.6 Hz), 0.78 (3H, d, J=6.7 Hz), 1.52–1.65 (2H, m), 1.91–2.03 (2H, m), 2.24–2.31 (4H, m), 2.67 (3H, s), 3.03–3.13 (2H, m), 3.32–3.42 (1H, m), 3.46–3.51 (1H, m), 3.59–3.71 (2H, m), 4.16 (1H, dd, J=6.8 and 2.2 Hz), 5.11 (1H, s), 7.00 (1H, d, J=7.5 Hz), 7.13–7.18 (2H, m), 7.26 (1H, t, J=7.7 Hz), 7.46 (1H, t, J=7.0 Hz), 7.64–7.73 (2H, m), 7.76 (1H, d, J=7.5 Hz).

EXAMPLE 11

N-[2,3-Dihydro-1-(2-methylpropyl)-2-oxo-5-(piperidin-4-yl)- 1H-1,4-benzodiazepin-3-yl]-N'-[3-(tetrazol-5-yl)phenyl]urea, trifluoroacetic acid salt 1. 5-(3-Nitrophenyl)tetrazole To a solution of 3-cyanonitrobenzene-(20 g, 0.13 mol) in 1-methyl-2-pyrrolidinone (200 ml) was added triethylamine hydrochloride (27.9 g, 0.20 mol) followed by sodium azide (26.4 g, 0.40 mol). The mixture was heated at 160° C. for 1.5 h, then cooled to ambient temperature, poured into ice water (1000 ml) and acidified using 5M HCl. The solid which precipitated from the mixture was filtered, washed with water and dried under vacuum at 50° C. to afford the title tetrazole (22.1 g, 86%) as a beige powder; mp 154°–156° C; $\delta_H$ (360 MHz, CDCl$_3$), 7.59 (1H, t, J=9 Hz), 8.19 (1H, d, J=8 Hz), 8.36 (1H, d, J=8 Hz), 8.86 (1H, s).

2. 5-(3-Aminophenyl)tetrazole, hydrochloride salt

To a solution of 5-(3-nitrophenyl)tetrazole (22 g, 0.12 mol) in ethanol (500 ml) was added 10% palladium on carbon (1.5 g, 7% (w/w)) in hydrochloric acid (23 ml of a 5M solution). The mixture was hydrogenated at 40 psi for 10 min, then the catalyst filtered off and washed with water. The solvents were evaporated in vacuo and the brown solid azeotroped with toluene (4×100 ml). The resulting solid was triturated with hot ethanol to give 5-(3-aminophenyl)tetrazole hydrochloride (16.3 g, 71%) as a beige powder; mp 203°–205° C.; $\delta_H$ (360 MHz, D$_2$O) 7.63 (1H, d, J=9 Hz), 7.75 (1H, t, J=8 Hz), 8.00 (2H, m).

3. N-[5-(1, tert-Butyloxycarbonylpiperidin-4-yl)-2,3-dihydro-1-(2-methylpropyl)-2-oxo-1H-1,4-benzodiazepin-3-yl]-N'-[3-(tetrazol-5-yl)-phenyl]urea 5-(3-Aminophenyl)tetrazole hydrochloride salt (400 mg, 1.89 mmol) was suspended in anhydrous tetrahydrofuran (10 ml), under an atmosphere of nitrogen, and triethylamino (527 µl, 3.79 mmol) was added dropwise. The resultant suspension was then cooled to 0° C. and triphosgene (186 mg, 0.63 mmol) was added followed by triethylamino (263 µl, 1.89 mmol) in three portions. After 2 min more triethylamine (263 µl, 1.89 mmol) was added then the ice bath removed and the suspension stirred at room temperature for 30 min. A solution of 3-(R,S)-amino-5-(1-tert-butyloxycarbonylpiperidin-4-yl)- 1,3-dihydro-1-(2-methylpropyl)-2H-1,4-benzodiazepin-2-one (603 mg, 1.46 mmol) in anhydrous tetrahydrofuran (10 ml) was added and the reaction mixture stirred at room temperature for 1 h. The mixture was then diluted with ethyl acetate (15 ml) and acidified using 20% aqueous acetic acid. The organic phase was separated and the aqueous layer extracted with ethyl acetate (20 ml). The combined organic layers were washed with brine (50 ml), dried (Na$_2$SO$_4$) and evaporated in vacuo. The residue was chromatographed on silica gel, using dichloromethane-methanol-acetic acid (90:5:5) as the eluant to give the urea as a pale yellow solid. The yellow solid was recrystallized from methanol to afford the urea (0.62 g, 71%) as a white solid; mp 195° C. (dec.) (MeOH); $\delta_H$ (360 MHz, CDCl$_3$) 0.73 (3H, d, J=6.6 Hz), 0.81 (3H, d, J=6.8 Hz), 1.26–1.36 (1H, m), 1.44 (9H, s), 1.57–1.66 (2H, m), 1.72–1.82 (1H, m), 2.00–2.08 (1H, m), 2.72–2.85 (2H, m), 2.96–3.04 (1H, m), 3.46 (1H, dd, J=14.4 and 7.2 Hz), 4.04–4.14 (1H, m), 4.14–4.23 (1H, m), 4.30 (1H, dd, J=13.8 and 9.3 Hz), 5.29 (1H, d, J=7.3 Hz), 7.29–7.42 (5H, m), 7.50–7.65 (3H, m), 7.67–7.70 (1H, m), 8.05 (1H, br s), 8.96 (1H, br s).

4. N-[2,3-Dihydro-1-(2-methylpropyl)-2-oxò-5-(piperidin-4-yl)-1H, 1,4-benzodiazepin-3-yl]-N'-[3-(tetrazol-5-yl)phenyl]urea, trifluoroacetic acid salt To a solution of N-[5-(1-tert-butyloxycarbonylpiperidin-4-yl)- 2,3-dihydro-1-(2-methylpropyl)-2-oxo-1H, 1,4-benzodiazepin-3-yl]-N'-[3-(tetrazol-5-yl)phenyl]urea (506 mg, 0.84 mmol) in anhydrous dichloromethane (20 ml), under an atmosphere of nitrogen, was added trifluoroacetic acid The solution was stirred at room temperature for 1 h, after which time the solvent was evaporated in vacuo. The residue was triturated with toluene to afford a white solid The solid was recrystallized from methanol to afford the desired urea (72 mg, 14%) as a white solid Evaporation of the mother liquors afforded more of the title compound (410 mg, 79%) as a white solid; mp 208°–210° C. (MeOH); $\delta_H$ (360 MHz, DMSO-d$_6$) 0.64 (3H, d, J=6.6 Hz), 0.77 (3H, d, J=6.7 Hz), 1.38–1.52 (2H, m), 1.62–1.72 (1H, m), 1.76–1.90 (1H, m), 2.05–2.15 (1H, m), 2.88–3.00 (2H, m), 3.20–3.45 (3H, m), 3.65 (1H, dd, J=16.6 and 7.2 Hz), 4.17 (1H, dd, J=13.8 and 9.5 Hz), 5.09 (1H, d, J=7.5 Hz), 7.41–7.46 (4H, m), 7.55–7.57 (1H, m), 7.67–7.73 (2H, m), 7.81 (1H, d, J=6.8 Hz), 8.15 (1H, s), 9.28 (1H, s).

EXAMPLE 12

N-[2,3-Dihydro-5-(4,4-dimethylpiperidin-2-yl)-2-oxo-1-(1-propyl)-1H, 1,4-benzodiazepin-3-yl-N'-[5-indanyl]urea hydrochloride. Diastereomer B.

The title compound free base was prepared from Intermediate 6 following a similar method to that described for Example 1 (steps 1 and 2) except that 5-indanyl isocyanate was used instead for m-tolyl isocyanate; the hydrochloride salt was prepared and recrystallized from dichloromethane-diethyl ether; mp 170° C. (dec); $\delta_H$ (360 MHz, CDCl$_3$) 10.51 (1H, s), 9.14–9.02 (2H, m), 8.76–8.60 (1H, m), 7.84 (1H, dd, J=7.9 and 1.2 Hz), 7.54 (1H, dt, J=7.2 and 1,4 Hz), 7.35 (1H, d, J=8.2 Hz), 7.32–7.22 (3H, m), 6.94 (1H, d, J=8.0 Hz), 5.42 (1H, d, J=8.6 Hz), 4.36–4.20 (2H, m), 3.54–3.44 (1H, m), 3.12–2.90 (2H, m), 2.82–2.68 (4H, m), 2.00–1.87 (2H, m), 1.60–1.45 (1H, m), 1.34–1.10 (3H, m), 0.95–0.86 (4H, m and s), 0.73 (3H, t, J=7.4 Hz), 0.59 (3H, s), 0.48 (1H, t, J=13.5 Hz); m/z (CI), 488 (M$^+$+1). (Found: C, 65.31; H, 7.24; N, 12.97. C$_{29}$H$_{37}$N$_5$O$_2$×1.0HCl×0.5 H$_2$O requires: C, 65.34; H, 7.37; N, 13.14%).

EXAMPLE 13A

Tablets containing 1–25 mg of compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 13B

Tablets containing 26–100 mg of compound

|  | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 14

Parenteral injection

|  | Amount mg |
|---|---|
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 15

Topical formulation

|  | Amount mg |
|---|---|
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved The compound of formula (I) is added and stirring continued until dispersed The mixture is then cooled until solid.

BIOLOGICAL ACTIVITY

The CCK-A and CCK-B antagonising activity of the compounds described herein was evaluated using the assays described in published European patent application no. 0514133. The method essentially involves determining the concentration of the test compound required to displace 50% of the specific $^{125}$I—CCK from rat pancreas (CCK-A) or guinoa pig brain (CCK-B). The data in Table 1 were obtained for compounds of the Examples.

TABLE I

| | CCK RECEPTOR BINDING RESULTS | |
|---|---|---|
| | IC$_{50}$ (nM) | |
| Compound of Ex # | $^{125}$I-CCK Pancreas | $^{125}$I-CCK Brain |
| 1 | >3000 | 41.8 |
| 2 | >3000 | 36.4 |
| 3 | 2094 | 53.6 |
| 4 | 1514 | 15.4 |
| 5 | 3540 | 25.5 |
| 6 | 1385 | 12.0 |
| 7 | 6490 | 2.37 |
| 8 | 3087 | 1.47 |
| 9 | 2670 | 290 |
| 10 | 2930 | 240 |
| 11 | >3000 | 55 |
| 12 | 3218 | 0.89 |

We claim:

1. A compound of Formula (I), or a pharmaceutically acceptable salt or prodrug thereof:

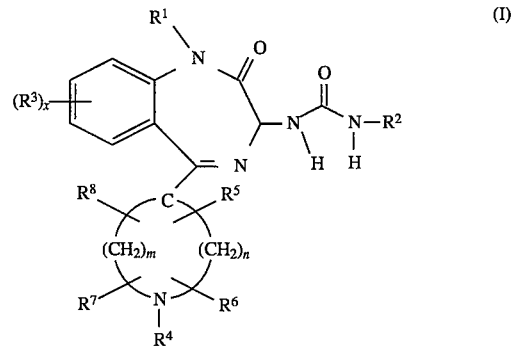

wherein:

$R^1$ represents $C_{1-6}$alkyl, $C_{3-7}$cycloalkyl, cyclopropylmethyl, $CH_2CO_2R^9$ (where $R^9$ is $C_{1-4}$alkyl) or $CH_2CONR^{13}R^{14}$, (where $R^{13}$ and $R^{14}$ each independently represents H or $C_{1-4}$alkyl, or $R^{13}$ and $R^{14}$ together form a chain $(CH_2)_p$ where p is 4 or 5);

$R^2$ represents a phenyl group optionally substituted by one or more substituents selected from $C_{1-6}$alkyl, halo, hydroxy, $C_{1-6}$alkoxy, $(CH_2)_q$ tetrazolyl optionally substituted in the tetrazole ring by $C_{1-4}$alkyl, $(CH_2)_q$ imidazolyl, $(CH_2)_q$triazolyl, (where q is 0, 1, 2 or 3), 5-hydroxy-4-pyrone, $NR^{13}R^{14}$ (where $R^{13}$ and $R^{14}$ are as previously defined), $NR^{10}COR^9$, $NR^{10}CONR^{10'}R^9$, (where $R^9$ is as previously defined and where $R^{10}$ and $R^{10'}$ are each independently H or $C_{1-6}$alkyl), $CONR^{13}R^{14}$ (where $R^{13}$ and $R^{14}$ are as previously defined), $SO(C_{1-6}$alkyl), $SO_2(C_{1-6}$alkyl), trifluoromethyl, $CONHSO_2R^{11}$, $SO_2NHCOR^{11}$, (where $R^{11}$ is $C_{1-6}$alkyl, optionally substituted aryl, 2,2-difluorocyclopropane or trifluoromethyl), $SO_2NHR^{12}$ (where $R^{12}$ is a nitrogen containing heterocycle), $B(OH)_2$, $(CH_2)_qCO_2H$ or $(CH_2)_qNR^{10}R^{12}$ (where q and $R^{10}$ are as previously defined and $R^{12}$ represents tetrazolyl optionally substituted by $C_{1-4}$alkyl; or $R^2$ represents a group

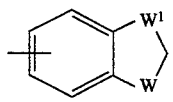

where W represents $CH_2$ or $NR^{10}$, where $R^{10}$ is as previously defined, and $W^1$ represents $CH_2$, or W and $W^1$ each represent O;

$R^3$ represents $C_{1-6}$alkyl, halo or $NR^{13}R^{14}$, where $R^{13}$ and $R^{14}$ are as previously defined;

$R^4$ represents H, $C_{1-4}$alkyl, optionally substituted phenyl or benzyl optionally substituted in the phenyl ring, where the phenyl substituents are selected from $C_{1-4}$alkyl, $C_{1-4}$alkoxy, halo and trifluoromethyl;

$R^5$, $R^6$, $R^7$ and $R^8$ each independently represent H or $C_{1-4}$alkyl; or any two of $R^4$, $R^5$, $R^6$, $R^7$ and $R^8$ together form a chain $(CH_2)_t$, and any other two or $R^4$, $R^5$, $R^6$, $R^7$ and $R^8$ optionally form a chain $(CH_2)_s$ where s and t are independently 1, 2 or 3;

m is 2, 3, 4, 5, 6, 7, 8 or 9;

n is 0, 1, 2, 3 or 4; and x is 0, 1, 2 or 3.

2. A compound as claimed in claim 1 wherein $R^4$ represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl; $R^5$ and $R^6$ each independently represent H or $C_{1-4}$alkyl, or $R^5$ and $R^6$ together form a chain $(CH_2)_t$, where t is 1, 2 or 3; and $R^7$ and $R^8$ are both H.

3. A compound as claimed in claim 2 of Formula (IA):

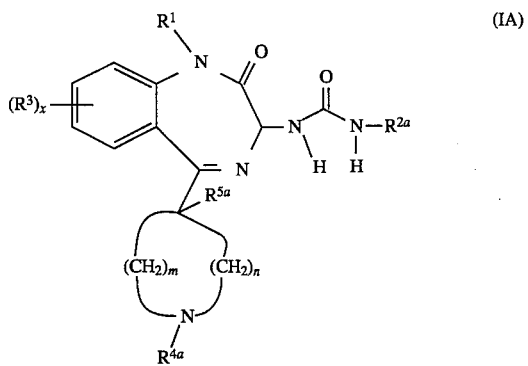

wherein $R^1$, $R^3$, m, n and x are as defined for Formula (I);

$R^{2a}$ represents a phenyl group optionally substituted by one or more substituents selected from $C_{1-6}$alkyl, halo, hydroxy, $C_{1-4}$alkoxy, $(CH_2)_q$tetrazolyl optionally substituted in the tetrazole ring by $C_{1-4}$alkyl, $(CH_2)_q$imidazolyl, $(CH_2)_q$triazolyl, 5hydroxy-4-pyrone, $NR^{13}R^{14}$, $NR^{10}COR^9$, $NR^{10}CONR^{10'}$-$R^9$, $CONR^{13}R^{14}$, $SO(C_{1-6}$alkyl), $SO_2(C_{1-6}$alkyl), trifluoromethyl, $CONHSO_2R^{11}$, $SO_2NHCOR^{11}$, $SO_2NHR^{12}$, $B(OH)_2$ and $(CH_2)_rCO_2H$, where r is zero, 1 or 2; or $R^{2a}$ represents a group

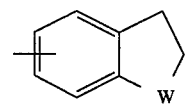

where W represents $CH_2$ or $NR^{10}$;

$R^{4a}$ represents H, $C_{1-4}$alkyl, optionally substituted phenyl or benzyl optionally substituted in the phenyl ring, where the phenyl substituents are selected from $C_{1-4}$alkyl, $C_{1-4}$alkoxy, halo and trifluoromethyl; and $R^{5a}$ represents H or $C_{1-4}$alkyl.

4. A compound as claimed in claim 1 wherein $R^1$ represents $C_{1-6}$alkyl.

5. A compound as claimed in claim 1 wherein $R^2$ represents phenyl substituted by one or two substituents selected from $C_{1-6}$alkyl, halo, trifluoromethyl and tetrazolyl, or $R^2$ represents 5-indanyl.

6. A compound as claimed in claim 1 wherein $R^4$ is H or methyl, m is 2, 4, 5 or 6 and n is 0 or 2.

7. A compound as claimed in claim 1 of Formula (IB):

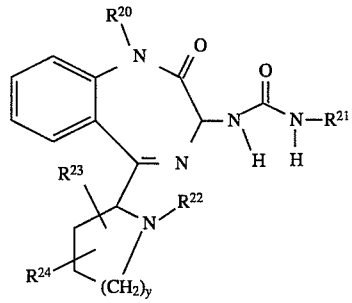

wherein $R^{20}$ is $C_{1-6}$alkyl;

$R^{21}$ is 5-indanyl or phenyl substituted by $C_{1-6}$alkyl, halo, trifluoromethyl or tetrazolyl;

$R^{22}$ is H or $C_{1-6}$alkyl;

$R^{23}$ and $R^{24}$ each represent H or methyl or $R^{23}$ and $R^{24}$ together form a chain $(CH_2)_s$ where s is 1 or 2; and Y is 2 or 3.

8. A compound as claimed in claim 1 selected from:

N-[2,3-dihydro-2-oxo-5-(piperidin-2-yl)-1-(1-propyl)-1H-1,4-benzodiazepin-3-yl]-N'-[3-methylphenyl]urea;

N-[2,3-dihydro-5-(1-methylpiperidin-2-yl)-2-oxo-1-(1-propyl)-1H- 1,4-benzodiazepin-3-yl]-N'-[3-methylphenyl]urea;

N-[2,3-dihydro-5-(5,5-dimethyl-2,3,4,5,6-hexahydro-1H-azepin-2-yl)-2-oxo-1-(1-propyl)-1H-1,4-benzodiazepin-3-yl]-N'-[3-methylphenyl]urea;

N-[2,3-dihydro-5-(2,3,4,5,6-hexahydro-1,5,5-trimethyl-1H-azepin-2-yl)-2-oxo-1-(1-propyl)-1H-1,4-benzodiazepin-3-yl]-N'-[3-methylphenyl]urea;

N-[2,3-dihydro-5-(5,5-dimethyl-2,3,4,5,6-hexahydro-1H-azepin-2-yl)-1-methyl-2-oxo-1H-1,4-benzodiazepin-3-yl]-N'-[3-methylphenyl]urea;

N-[2,3-dihydro-5-(5,5-dimethyl-2,3,4,5,6-hexahydro-1H-azepin- 2-yl)-1-methyl-2-oxo-1H-1,4-benzodiazepin-3-yl]-N'-[5-indanyl]urea;

N-[2,3-dihydro-5-(4,4-dimethylpiperidin-2-yl)-2-oxo-1-(1-propyl)- 1H-1,4-benzodiazepin-3-yl]-N'-[3-methylphenyl]urea;

N-[2,3-dihydro-1-(2-methylpropyl)-2-oxo-5-(piperidin-4-yl)- 1H-1,4-benzodiazepin-3-yl]-N'-[3-methylphenyl]urea;

N-[2,3-dihydro-5-(N-methylpiperidin-4-yl)-1-(2-methylpropyl)- 2-oxo-1H-1,4-benzodiazepin-3-yl]-N'-[3-methylphenyl]urea;

N-[2,3-dihydro-1-(2-methylpropyl)-2-oxo-5-(piperidin-4-yl)-1H-1,4-benzodiazepin-3-yl]-N'-[3-(tetrazol-5-yl)phenyl]urea;

N-[2,3-dihydro-5-(4,4-dimethylpiperidin-2-yl)-2-oxo-1-(1-propyl)-1H-1,4-benzodiazepin-3-yl]-N'-[5-indanyl]urea.

9. A pharmaceutical composition comprising a compound as claimed in claim 1 in association with a pharmaceutically acceptable carrier.

10. A method for the treatment or prevention of a physiological disorder involving CCK and/or gastrin, which method comprises administration to a patient in need thereof a CCK and/or gastrin reducing amount of a compound according to claim 1.

11. A method as claimed in claim 10 for the treatment or prevention of anxiety.

12. A method as claimed in claim 10 for the treatment or prevention of panic.

13. A method as claimed in claim 10 for the treatment or prevention of pain.

14. A compound as claimed in claim 1 of Formula (I) wherein any two of $R^4$, $R^5$, $R^6$, $R^7$ and $R^8$ together form a chain $(CH_2)_t$, and any other two of $R^4$, $R^5$, $R^6$, $R^7$ and $R^8$ optionally form a chain $(CH_2)_s$ where s and t are independently 1, 2 or 3, which can result in the following structures in the 5-position of the benzodiazepine ring:

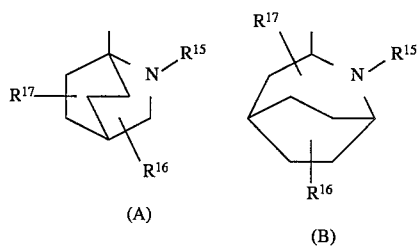

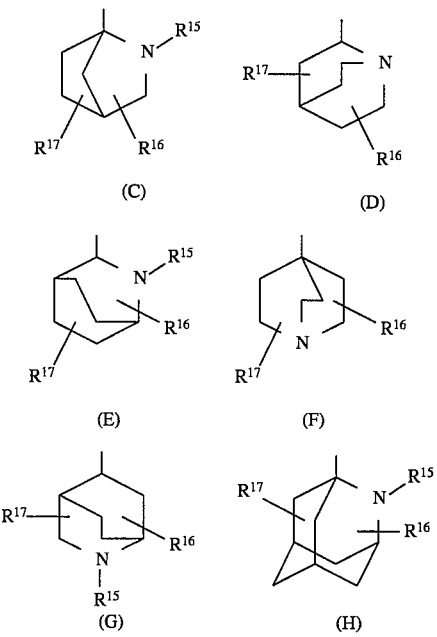

wherein $R^{15}$ represents H, $C_{1-4}$alkyl, phenyl or benzyl, in which either the phenyl or benzyl can be optionally substituted in the phenyl ring by a substituent selected from the group consisting of: $C_{1-4}$alkyl, $C_{1-4}$alkoxy, halo and trifluoromethyl; and $R^{16}$ and $R^{17}$ each represent H or $C_{1-4}$alkyl.

* * * * *